(12) United States Patent
Cooper-White et al.

(10) Patent No.: US 9,931,629 B2
(45) Date of Patent: Apr. 3, 2018

(54) SUBSTANCE EXPOSURE APPARATUS

(75) Inventors: Justin John Cooper-White, Upper Brookfield (AU); Drew Murray Titmarsh, Paddington (AU)

(73) Assignee: The University of Queensland, St Lucia, Queensland (AU)

( * ) Notice: Subject to any disclaimer, the term of this patent is extended or adjusted under 35 U.S.C. 154(b) by 784 days.

(21) Appl. No.: 14/428,204

(22) PCT Filed: Sep. 13, 2012

(86) PCT No.: PCT/AU2012/001094
§ 371 (c)(1),
(2), (4) Date: Jun. 26, 2015

(87) PCT Pub. No.: WO2013/036997
PCT Pub. Date: Mar. 21, 2013

(65) Prior Publication Data
US 2015/0298121 A1 Oct. 22, 2015

(30) Foreign Application Priority Data
Sep. 14, 2011 (AU) ................ 2011903773

(51) Int. Cl.
*B01L 3/00* (2006.01)
*B01F 5/06* (2006.01)
(Continued)

(52) U.S. Cl.
CPC .......... *B01L 3/5025* (2013.01); *B01F 5/0647* (2013.01); *B01F 13/0059* (2013.01);
(Continued)

(58) Field of Classification Search
CPC ............... B01F 13/0059; B01F 5/0647; B01L 2200/0642; B01L 2200/0694;
(Continued)

(56) References Cited

U.S. PATENT DOCUMENTS

| 2002/0124896 | A1 | 9/2002 | O'Connor et al. |
| 2003/0138973 | A1 | 7/2003 | Wagner et al. |

(Continued)

FOREIGN PATENT DOCUMENTS

| CN | 101165161 | 4/2008 |
| CN | 101629143 A | 1/2010 |

(Continued)

OTHER PUBLICATIONS

Notification of the First Office Action dated Mar. 24, 2016, issued in Chinese Patent Application No. 201280076891.8 and partial English translation.
(Continued)

*Primary Examiner* — Michael L Hobbs
(74) *Attorney, Agent, or Firm* — Nixon & Vanderhye P.C.

(57) ABSTRACT

An apparatus including an array of wells including a number of well channels, each well channel including a plurality of wells in the well channel, the wells containing a substance in use, one or more inlets for receiving respective fluids and channels coupled to the one or more inlets for selectively supplying one or more fluids to each well channel to thereby expose the substance to different conditions allowing a response of the substance to the conditions to be determined.

20 Claims, 19 Drawing Sheets

(51) Int. Cl.
*B01F 13/00* (2006.01)
*C12M 1/32* (2006.01)
*C12M 1/12* (2006.01)
*C12M 1/02* (2006.01)

(52) U.S. Cl.
CPC ........... *B01L 3/5027* (2013.01); *C12M 23/12* (2013.01); *C12M 25/00* (2013.01); *C12M 27/00* (2013.01); *B01L 2200/026* (2013.01); *B01L 2200/0642* (2013.01); *B01L 2200/0694* (2013.01); *B01L 2200/10* (2013.01); *B01L 2300/041* (2013.01); *B01L 2300/087* (2013.01); *B01L 2300/0816* (2013.01); *B01L 2300/0829* (2013.01); *B01L 2300/0861* (2013.01); *B01L 2300/0864* (2013.01); *B01L 2300/0867* (2013.01); *B01L 2300/0874* (2013.01); *B01L 2300/0883* (2013.01); *B01L 2300/0893* (2013.01); *B01L 2300/12* (2013.01); *B01L 2300/16* (2013.01); *B01L 2400/0694* (2013.01); *B01L 2400/082* (2013.01)

(58) Field of Classification Search
CPC ........... B01L 2200/10; B01L 2300/041; B01L 2300/0816; B01L 2300/0829; B01L 2300/0861; B01L 2300/0864; B01L 2300/087; B01L 2300/0874; B01L 2300/0883; B01L 2300/0893; B01L 2300/12; B01L 2300/16; B01L 2400/0694; B01L 2400/082; B01L 3/5025; B01L 3/5027; C12M 23/12; C12M 25/00; C12M 27/00
See application file for complete search history.

(56) References Cited

U.S. PATENT DOCUMENTS

2005/0266582 A1* 12/2005 Modlin ............. B01L 3/502723
436/164
2007/0099294 A1* 5/2007 Yang ..................... C12M 25/14
435/299.1
2007/0151942 A1 7/2007 Dishongh et al.

FOREIGN PATENT DOCUMENTS

| EP | 1 544 287 A1 | 6/2005 |
|---|---|---|
| JP | 2004-81019 A | 3/2004 |
| JP | 2007-504816 A | 3/2007 |
| JP | 2008-233002 A | 10/2008 |
| JP | 2009-042103 A | 2/2009 |
| JP | 2012-118039 A | 6/2012 |
| WO | 2005/023124 A2 | 3/2005 |
| WO | 2007/008609 A2 | 1/2007 |
| WO | 2009/024595 A2 | 2/2009 |
| WO | 2010/024779 A1 | 3/2010 |
| WO | WO 2010/024779 | 3/2010 |
| WO | 2011/107519 A2 | 9/2011 |
| WO | WO 2011/135339 | 11/2011 |
| WO | 2011/161480 A1 | 12/2011 |
| WO | WO 2011/161480 | 12/2011 |

OTHER PUBLICATIONS

Extended European Search Report dated Apr. 1, 2016, issued in European Patent Application No. 12831505.8.
Notice of Reasons for Rejection dated Jul. 4, 2016, issued in Japanese Patent Application No. 2015-531403 and partial English Translation.
International Preliminary Report on Patentability with Written Opinion for PCT/AU2012/001094, dated Mar. 17, 2015, 8 pages.
International Search Report for PCT/AU2012/001094, dated Nov. 26, 2012, four pages.
Written Opinion of the ISA for PCT/AU2012/001094, dated Nov. 26, 2012, seven pages.
English translation of Notice of Reasons for Rejection dated May 22, 2017, issued in Japanese Patent Application No. 2015-531403.

\* cited by examiner

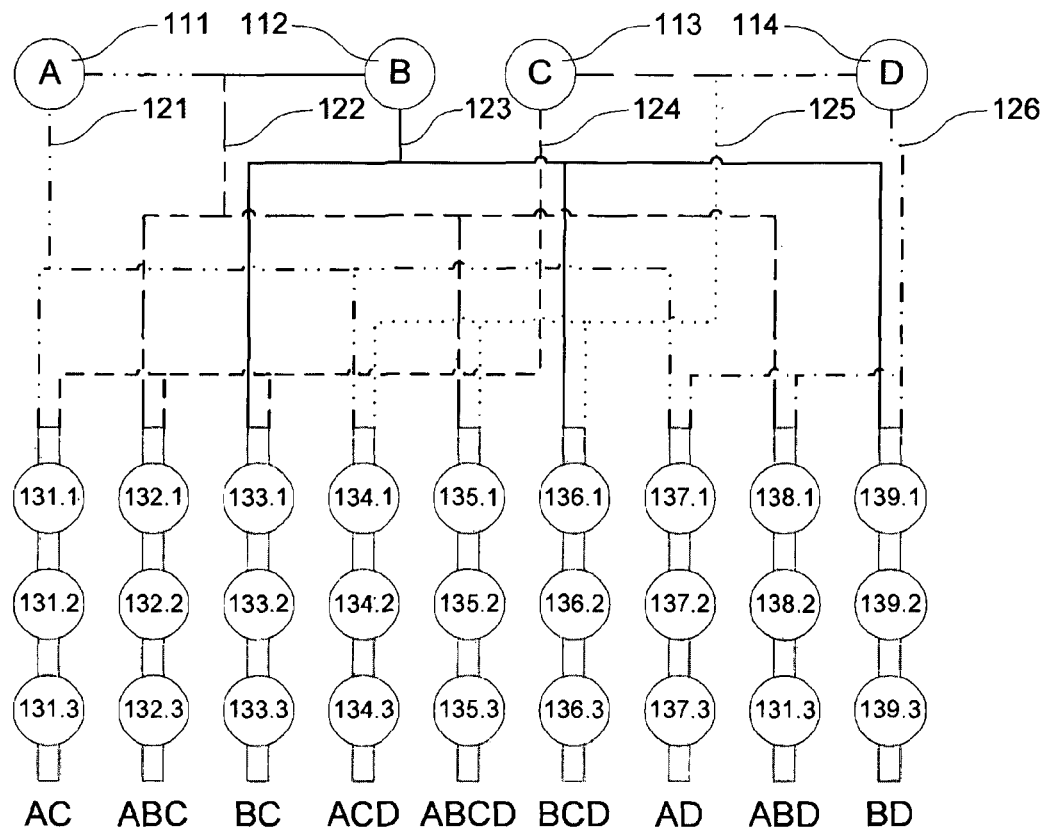
Fig. 1C
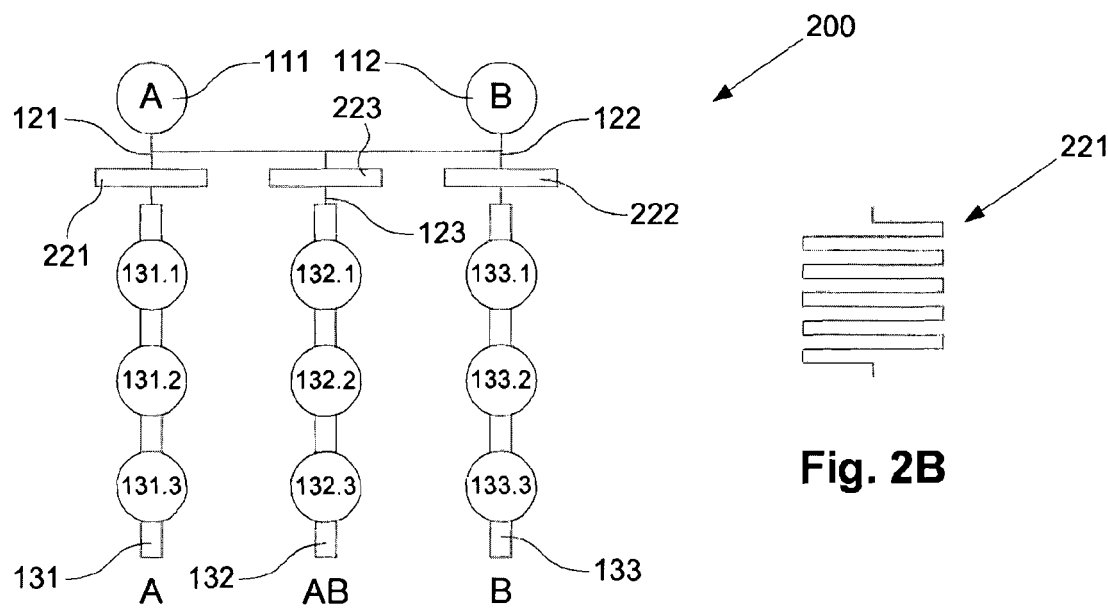
Fig. 2A
Fig. 2B

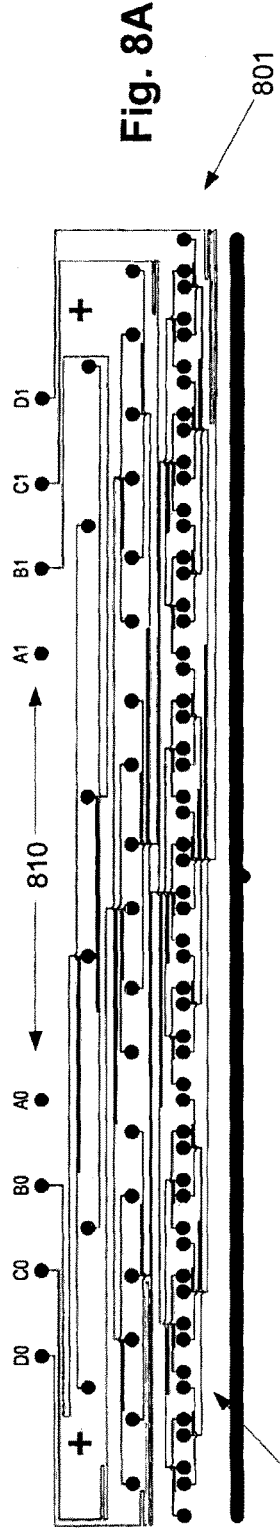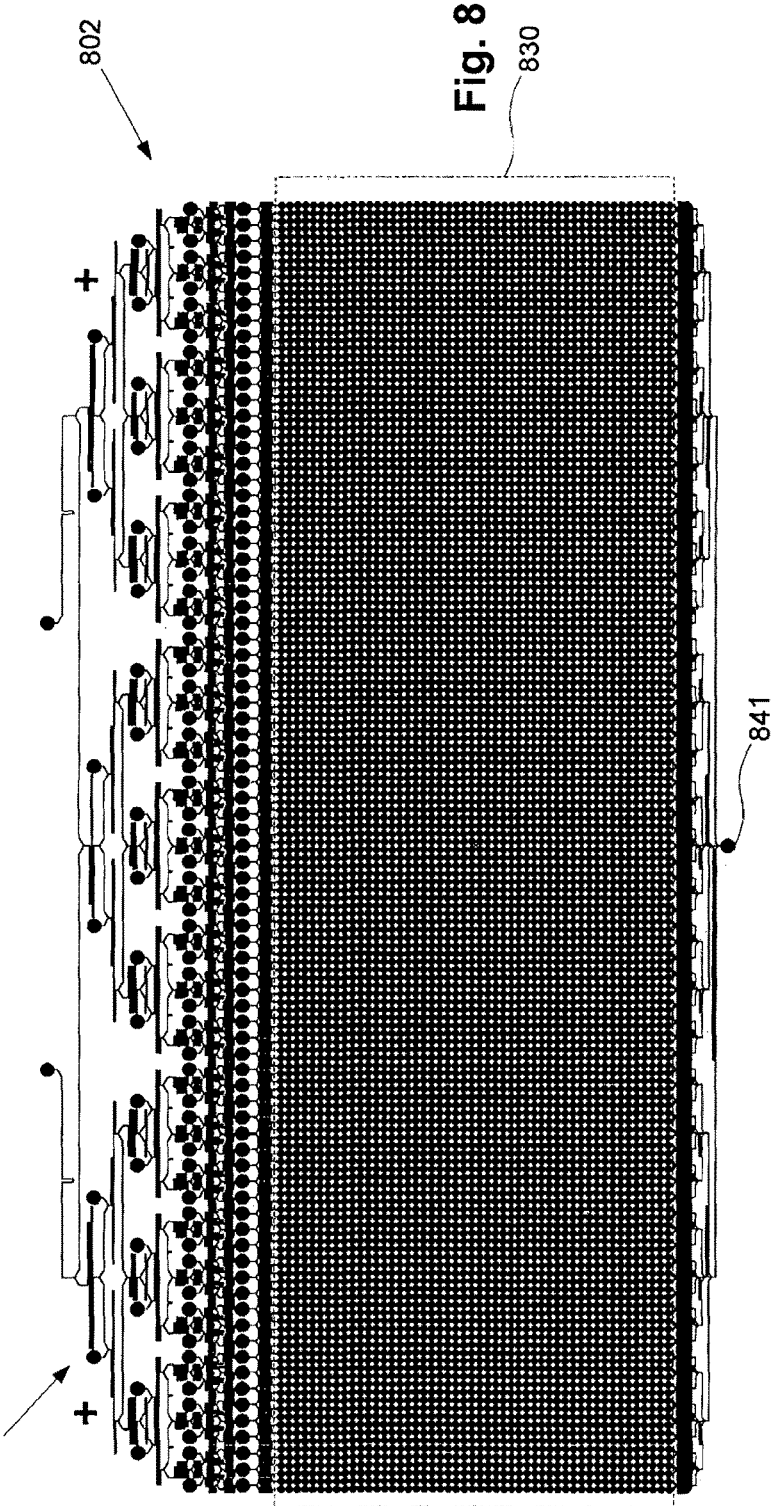

SUBSTANCE EXPOSURE APPARATUS

This application is the U.S. national phase of International Application No. PCT/AU2012/001094 filed 13 Sep. 2012 which designated the U.S., the entire content of which is hereby incorporated by reference.

BACKGROUND OF THE INVENTION

The present invention relates to an apparatus and method for exposing a substance to conditions, and in particular, to a method and apparatus for exposing a substance, such as cells, to a range of different conditions, to thereby allow a response of the substance to the conditions to be determined.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Pluripotent stem cells are promising cell sources for production of specialised cell types useful for cell transplantation, modelling of disease and development, and for preclinical drug screening. However, the use of human pluripotent stem cells (hESC and hIPS cells) in regenerative medicine and drug screening applications is predicated on the ability to direct both their undifferentiated expansion to sufficient numbers, and efficient lineage-specific differentiation to target phenotypes. Throughout early development the exposure of stem cells to gradients of micro-environmental stimuli determines cellular fate decisions leading to patterning of heterogeneous, organised tissues.

Therefore, precise knowledge and control of these stimuli is important to deconstruct the hierarchical nature of complex developmental processes and identify the key stimuli which directly and efficiently drive specification and regulation of defined cell populations. Yet, several issues currently obstruct efforts to achieve these goals.

It is well established that the balance between activities of multiple signalling pathways is central in determining cellular fate outcomes, and is highly dependent on the relative levels of extrinsic signals, and not just presence or absence of certain factors. Approaches which screen various relative levels of multiple stimuli are therefore required, rather than simply optimising individual stimuli. Also, conventional, static culture systems are unsuitable for accurately probing micro-environmental stimuli that direct stem cell fate.

Historical use of serum-containing media and feeder layers has introduced undefined components to stem cell culture systems, but even in feeder-free, defined culture conditions hESCs secrete factors that are known to impact self-renewal and differentiation outcomes, which also change dynamically after the onset of differentiation. Moreover, conventional cultures are subjected to considerable spatio-temporal fluctuation in micro-environmental conditions, as secreted factors and wastes are accumulated and exogenous factors and nutrients are depleted, but then revert to initial conditions when medium is replenished.

Microscale technologies have been utilised to investigate a range of biological phenomena. To date, studies on arrayed microenvironments have utilised high-density spotting approaches to pattern molecules of interest, and include combinatorial arrays of biomaterial polymers or extracellular matrix (ECM) molecules, optionally with introduction of various soluble factors, either by coupling of arrays to macroscale wells, or by inclusion of spotted soluble factors in the array. Although these approaches readily present ECM cues, the level of control of soluble factor presentation is limited. Where soluble factors are added to a macroscale culture volume, the microenvironmental control is limited by the batch culture environment which exists between medium changes. On the other hand, while the spotted soluble factors display signalling activity, transport phenomena such as diffusion from the substratum and diffusion/convection throughout the medium volume mean the exact concentrations of soluble factors being presented to cells are hard to define and time-variable.

"Closed" culture systems such as those embodied in microfluidic devices have previously been combined with perfusion culture to achieve controlled provision of soluble factors and temporal variation of conditions with good time resolution.

For example, multiplexed integration of 96 discrete, individually-addressable microbioreactor chambers with application to screening of culture environments for mesenchymal stem cell growth and differentiation is described in Gómez-Sjöberg, R., Leyrat, A. A., Pirone, D. M., Chen, C. S. & Quake, S. R. Versatile, Fully Automated, Microfluidic Cell Culture System. Analytical Chemistry 79, 8557-8563 (2007). This device however required 73 off-chip connections and could not provide continuous perfusion to multiple chambers, although rapid exchanges of medium were possible. Nevertheless, microfabrication technology can be leveraged to be extensively multiplexed and generate a large spectrum of conditions based on a limited number of compounds.

Recent advances in multiplexed array technology for microenvironmental screening have focused on spotted combinatorial arrays of biomaterial polymers. Although these approaches are ideally suited to, and readily present ECM cues, the level of control of soluble factor presentation is still limited. Where soluble factors are added to a macroscale culture volume, the microenvironmental control is limited by the points detailed above. On the other hand, while the spotted soluble factors undoubtedly display signalling activity, transport phenomena such as diffusion from the substratum and diffusion/convection throughout the medium volume mean the exact concentrations of soluble factors being presented to cells are often hard to define and are also time-variable.

"Microbioreactor Array for Full-Factorial Analysis of Provision of Multiple Soluble Factors in Cellular Microenvironments" Biotechnology and Bioengineering, Vol. 104, No. 6, Dec. 15, 2009 describes a scalable microbioreactor architecture that uses nested dilution structures to generate a full-factorial array of cell culture conditions. However, the arrangement provides only limited ability to assess the impact of events such as paracrine signalling.

SUMMARY OF THE PRESENT INVENTION

In a first broad form the present invention seeks to provide an apparatus for exposing a substance to conditions, the apparatus including:
  a) an array of wells including a number of well channels, each well channel including a plurality of wells in the well channel, the wells containing a substance in use;
  b) one or more inlets for receiving respective fluids; and,
  c) channels coupled to the one or more inlets for selectively supplying one or more fluids to each well channel to thereby expose the substance to different conditions allowing a response of the substance to the conditions to be determined.

Typically each well channel includes a plurality of wells spaced apart along the well channel Typically the fluid supplied to a first end of the well channel flows along the well channel to a second end of the well channel in a flow direction.

Typically a response in at least one well influences conditions in an adjacent well.

Typically at least some agents produced in a well are transferred to an adjacent well to thereby at least partially alter the conditions in the adjacent well.

Typically the apparatus includes:
  a) at least two inlets, each inlet being for receiving a respective fluid; and,
  b) a number of channels for supplying the respective fluids from the inlets to the well channels, each channel having a respective channel geometry to, thereby control a relative flow of fluids so that respective proportions of the fluids are supplied to each well channel.

Typically for fluid flow in a flow direction, agents produced by substances in an upstream well are transferred to a downstream well.

Typically for no fluid flow, agents are transferred between wells by diffusion.

Typically a well channel geometry of each channel is arranged so that each well channel receives at least one of:
  a) an equal volume of fluid;
  b) an equal flow of fluid; and,
  c) equal proportions of fluid.

Typically the channel geometry includes at least one of:
  a) a channel shape;
  b) a channel tortuousity;
  c) a channel length;
  d) a channel height;
  e) a channel width;
  f) a channel angle; and,
  g) obstructions within the channel.

Typically at least one channel divides to supply fluid to at least two well channels.

Typically at least two channels combine to supply a mixture of fluids to at least one well channel.

Typically the channels include mixing portions for mixing fluids contained therein.

Typically at least two channels combine upstream of a mixing portion.

Typically the apparatus includes first and second inlets for receiving respective first and, second fluids, and wherein the channels are arranged so that:
  i) at least one well channel receives the first fluid;
  ii) at least one well channel receives the second fluid; and,
  iii) at least one well channel receives a mixture of the first and second fluids.

Typically the apparatus includes first and second inlets for receiving respective first and second fluids, the first fluid including a factor and the second fluid including a buffer so that different well channels receive different concentrations of the factor.

Typically the apparatus includes, a number of inlet sets, each inlet set including at least two inlets, and each inlet set being for receiving respective fluids.

Typically each inlet sets receives a fluid including a respective factor.

Typically the apparatus includes:
  a) a number (n) of inlet sets, each including at least two inlets, resulting in a total of at least 2n inlets; and,
  b) a number (n) of inlet sets, each containing at least 2 inlets, where 1 inlet from each inlet set is further joined to a common inlet, resulting in a total of at least n+1 inlets.

Typically the apparatus includes:
  a) a first inlet set for receiving a first factor and a buffer;
  b) a second inlet set for receiving a second factor and a buffer;
  c) a third inlet set for receiving a third factor and a buffer and wherein each well channel receives a respective concentration of each of the first, second and third factors.

Typically the fluids from one inlet set are combined by mixing with the fluids of a subsequent inlet set, thereby combining the respective fluids.

Typically the apparatus includes:
  a) at least one seeding inlet for receiving a seeding fluid containing the substance; and,
  b) at least one seeding outlet, the at least one seeding inlet and seeding outlet being in fluid communication with the well channels, thereby allowing the wells to be seeded with the substance.

Typically apparatus includes a number of seeding channels for connecting at least one of the at least seeding inlet and the at least one seeding outlet to the well channels.

Typically the at least one seeding inlet is connected to an opposing end of the well channels to the at least one seeding outlet.

Typically seeding outlet is in fluid communication with the channels, and wherein the seeding outlet is arranged to be blocked after seeding of the well channels, thereby allowing the respective fluids to be supplied to the well channels.

Typically the apparatus includes at least one control device for selectively controlling at least one of:
  a) supply of fluid to at least one of a well channel and a well; and,
  b) sampling of fluid and/or substances from at least one of a well channel and a well.

Typically the control device includes a valve for selectively blocking a channel.

Typically the channels are microfluidic channels.

Typically the apparatus includes a substrate and a cover layer.

Typically the cover layer includes a first and second layer, and wherein at least some inlets are provided in the second layer for supplying respective fluids to channels in the first layer.

Typically the channels are defined in the cover layer.

Typically the wells are defined in at least one of the substrate and the cover layer.

Typically the cover layer includes a moulded polymeric material.

Typically the substrate and cover layer are coupled using at least one of:
  a) adhesive coupling;
  b) thermal coupling;
  c) mechanical coupling;
  d) plasma coupling;
  e) covalent/chemical coupling;
  f) electrostatic coupling; and,
  g) magnetic coupling.

Typically at least the wells are coated.

Typically the coatings include at least one of:
  a) a promoter;
  b) an inhibitor;
  c) a growth factor;

d) a clotting factor;
e) a hormone;
f) a signalling agent;
g) chemical compositions;
h) a drug;
i) a protein;
j) a ligand;
k) an antibody;
l) an organism;
m) cells;
n) mini-cells;
o) synthetic cells;
p) a liposome;
q) a micelle;
r) a polymeric micelle (polymersome)
s) a lipid;
t) a polymer;
u) a surfactant;
v) a fatty acid;
w) an ionic solution;
x) an acidic or basic solution;
y) a detection reagent;
z) a DNA molecule;
aa) an RNA molecule;
bb) a construct encoding a DNA or RNA sequence;
cc) a nucleotide;
dd) a nucleoside;
ee) a polypeptide;
ff) an amino acid;
gg) a viral particle;
hh) a plasmid;
ii) a nanoparticle;
jj) a microparticle;
kk) a magnetic particle;
ll) conditioned medium;
mm) a fraction purified from conditioned medium;
nn) a natural extract;
oo) a culture medium component;
pp) a cell culture additive;
qq) a carbohydrate;
rr) a vitamin;
ss) a metabolite;
tt) an oligonucleotide;
uu) a fusion protein;
vv) a proteoglycan; and,
ww) a pathogen.
Typically at least one fluid includes an agent.
Typically the agent includes at least one of:
a) a promoter;
b) an inhibitor;
c) a growth factor;
d) a clotting factor;
e) a hormone;
f) a signalling agent;
g) chemical compositions;
h) a drug;
i) a protein;
j) a ligand;
k) an antibody;
l) an organism;
m) cells;
n) mini-cells;
o) synthetic cells;
p) a liposome;
q) a micelle;
r) a polymeric micelle (polymersome)
s) a lipid;
t) a polymer;
u) a surfactant;
v) a fatty acid;
w) an ionic solution;
x) an acidic or basic solution;
y) a detection reagent;
z) a DNA molecule;
aa) an RNA molecule;
bb) a construct encoding a DNA or RNA sequence;
cc) a nucleotide;
dd) a nucleoside;
ee) a polypeptide;
ff) an amino acid;
gg) a viral particle;
hh) a plasmid;
ii) a nanoparticle;
jj) a microparticle;
kk) a magnetic particle;
ll) conditioned medium;
mm) a fraction purified from conditioned medium;
nn) a natural extract;
oo) a culture medium component;
pp) a cell, culture additive;
qq) a carbohydrate;
rr) a vitamin;
ss) a metabolite;
tt) an oligonucleotide;
uu) a fusion protein;
vv) a proteoglycan; and,
ww) a pathogen.
Typically the substance includes at least one of:
a) a promoter;
b) an inhibitor;
c) a growth factor;
d) a clotting factor;
e) a hormone:
f) a signalling agent;
g) chemical compositions;
h) a drug;
i) a protein;
j) a ligand;
k) an antibody;
l) an organism;
m) cells;
n) mini-cells;
o) synthetic cells;
p) a liposome;
q) a micelle;
r) a polymeric micelle (polymersome)
s) a lipid;
t) a polymer;
u) a surfactant;
v) a fatty acid;
w) an ionic solution;
x) an acidic or basic solution;
y) a detection reagent;
z) a DNA molecule;
aa) an RNA molecule;
bb) a construct encoding a DNA or RNA sequence;
cc) a nucleotide;
dd) a nucleoside;
ee) a polypeptide;
ff) an amino acid;
gg) a viral particle;
hh) a plasmid;
ii) a nanoparticle;
jj) a microparticle;

kk) a magnetic particle;
ll) conditioned medium;
mm) a fraction purified from conditioned medium;
nn) a natural extract;
oo) a culture medium component;
pp) a cell culture additive;
qq) a carbohydrate;
rr) a vitamin;
ss) a metabolite;
tt) an oligonucleotide;
uu) a fusion protein;
vv) a proteoglycan; and,
ww) a pathogen.

Typically the apparatus is for monitoring at least one of:
a) response to agents;
b) cell growth;
c) cell differentiation;
d) cell viability;
e) cell morphology;
f) cell signalling;
g) protein translocation;
h) cell antigen presentation;
i) DNA synthesis;
j) cell genome;
k) cell transcriptome;
l) cell proteome;
m) cell metabolism;
n) cell electrophysiological function;
o) cell physiological function;
p) phagocytosis;
q) endocytosis;
r) gene expression;
s) protein expression;
t) carbohydrate expression;
u) biomolecular interactions;
v) receptor binding;
w) cell binding of a detection agent;
x) cell uptake of a modulation agent;
y) Cell migration;
z) Cell population organisation;
aa) Cell adhesion;
bb) Cell-cell interactions;
cc) Lipid expression;
dd) RNA synthesis; and,
ee) Tissue formation.

BRIEF DESCRIPTION OF THE DRAWINGS

An example of the present invention will now be described with reference to the accompanying drawings, in which:—

FIGS. 1A to 1C are schematic diagrams of examples of apparatus for modulating cell activity;

FIG. 2A is a schematic diagram of a further example of an apparatus for modulating cell activity;

FIG. 2B is a schematic diagram of the channel mixer portion of FIG. 2A in more detail;

DETAILED DESCRIPTION OF THE PREFERRED EMBODIMENTS

Figure 1A:
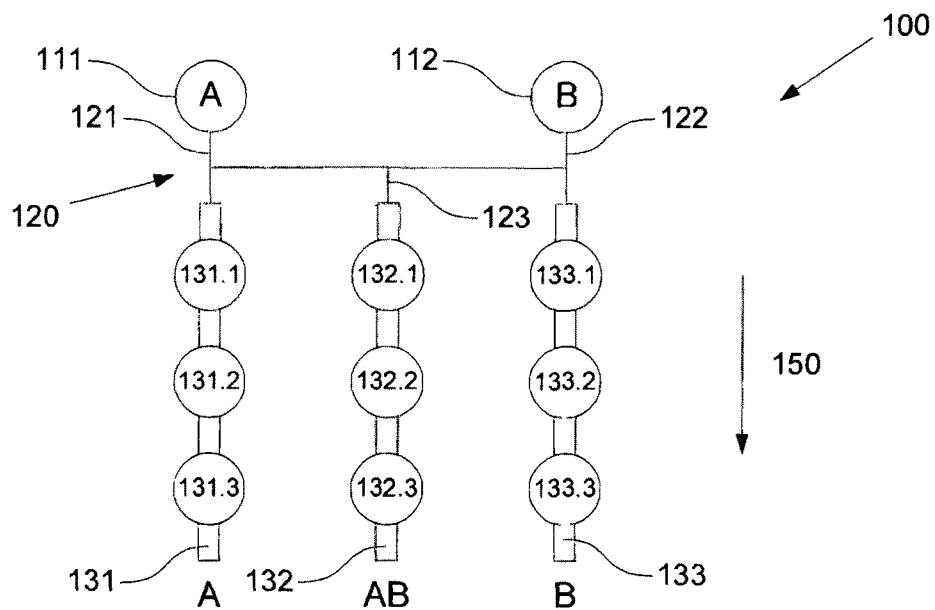

An example of apparatus for modulating cell activity will now be described with reference to FIG. 1A.

In this example, the apparatus 100 includes a well array 130 having a number of well channels 131, 132, 133, each well channel 131, 132, 133 including a plurality of wells 131.1, 131.2, 131.3, 132.1, 132.2, 132.3, 133.1, 133.2, 133.3, provided in, and typically spaced apart along, the well channel 131, 132, 133. In use, the wells 131.1, 131.2, . . . 133.3 contain a substance whose response to different conditions is to be determined.

In this example, three wells are shown on each well channel, and three well channels are shown, but it will be appreciated that this is for the purpose of example only, and in practice any number of wells and well channels can be used. The wells may be of any shape or size, such as circular, square, rectangular, oblong, triangular, or other geometric or non-geometric shape, and the use of circular wells is for the purpose of example only.

The apparatus 100 also includes one or more inlets 111, 112 for receiving one or more fluids, with two inlets being shown in this example.

The apparatus 100 also includes one or more inlets 111, 112 for receiving one or more fluids, with two inlets being shown in this example. The inlets 111, 112 are coupled via channels 120 to the well channels 131, 132, 133 allowing fluids to being selectively supplied to the well channels 131, 132, 133, thereby exposing the substance to different conditions, which in turn allows a response of the substance to the conditions to be determined.

The conditions to which samples are exposed can be controlled in a variety of ways. In one example, the conditions are dependent on the fluids supplied, with different fluids being supplied to different well channels. In this instance, substances in different well channels will therefore be exposed to different conditions, and accordingly the response of substances within the wells of different well channels can be compared to determine the response of the substance to the different conditions.

Alternatively, in another example, different substances can be provided in different well channels, with the different substances being exposed to the same or different conditions, depending for example on the fluids supplied to the well channels.

In a further example, the wells and/or well channels can be coated with one or more coatings. For example, the coatings could include binding agents to help the substance bind to a surface of the wells, marking agents for use in marking substances for detection purposes, other reagents, or the like. Example coatings include proteins, ligands, soluble factors, immobilized factors, lyophilised drugs or proteins, lentiviral particles, DNA, RNA, fluorescent probes, polymers, enzymes, or the like. The coatings can also have an impact on the conditions within the well, so that for example, different coatings could be applied to the wells in different well channels, allowing substances in the wells of different well channels to be exposed to different conditions, even if similar fluids are provided to the different well channels.

In any of the above examples, it is possible for secondary effects influencing conditions within wells to be induced. In this regard, when a substance is exposed to particular conditions, the response may include the production or modification of one or more agents, which can then be transferred to adjacent wells, thereby modifying the conditions in the adjacent well. Thus, for example, when cells are exposed to different conditions, the cells may be modulated so that they secrete agents, which are in turn transferred to different wells, thereby further modulating the cells contained therein. The modification can therefore mean that even under common starting conditions, the substances within different wells in a single well channel can be exposed to different conditions.

In one example, fluid is arranged to flow through the well channels in a flow direction. To achieve this, in this example, the inlets 111, 112 are in fluid communication with one end of the well channels, with fluids being selectively supplied to the end of the well channels 131, 132, 133, so that supplied fluid flows along the well channel to the other end of the well channel in a flow direction indicated by arrow 150. The other end of the well channels may be connected to one or more outlets allowing fluid to exit the well channels. The presence of outlets and the operation of the channels 120 to selectively transfer fluid to the well channels will be described in more detail below. In this instance, any agents produced or modified in a well may be transferred to a downstream well by the fluid flow.

The use of fluid flow is not essential however, and alternatively exposure of the substance may occur under conditions of no flow, in which case agents may be transferred through other transport mechanisms, such as diffusion. Alternatively fluid flow may selectively controlled, for example having fluid flow rates adjusted, alternatively having the flow stopped and/or reversed. Flow may also be selectively controlled for different wells and channels using control devices, such as control valves, as will be described in more detail below.

It will also be appreciated that different conditions could be induced using other mechanisms, such as selective heating or cooling of wells, selective exposure to radiation, or the like. For example, a heating or cooling could be applied to all the wells in a well channel, or alternatively could be applied to a common set (or row) of wells across different well channels, thereby further increasing the range of conditions to which substances are exposed.

Accordingly, it will be appreciated that the above described apparatus allows substances to be exposed to a wide range of conditions. In one example, the conditions are primarily controlled by supplying different combinations of fluids to different well channels, although additional and/or alternative control can be achieved by providing different coatings within different well channels. In any event, the apparatus allows a wide range of conditions to be generated using limited inputs, and further allows for secondary effects to be induced, with the response of a substance in one well modifying the conditions in one or more adjacent wells, thereby influencing the response of the substance in adjacent wells.

The apparatus may be used to expose a variety of different substances to different conditions. The apparatus is however ideally suited for exposing chemical and biological substances to different conditions, including, but not limited to cells, proteins, mini-cells, such as bacteria without any RNA or DNA, micelles, liposomes, nucleic acids, chemical compositions and drugs.

In the case of the substance being cells, typically at least one of the fluids includes an agent for inducing a response in the cells, and in particular a modulating agent that will modify the activity of cells, such as a cell fate modulator. The cell responses that can be monitored can include, but are not limited to cell growth, cell differentiation, cell viability, cell electrophysiological function, cell physiological function, cell binding of a detection agent, cell uptake of a modulation agent, response to detection agents, cell migration, cell population organisation, cell adhesion, cell-cell interactions, lipid expression, RNA synthesis, tissue formation, or the like.

Thus, for example, the apparatus could be used for optimising antibody binding, transfection efficiency, or the like. The apparatus can also be used to provide a readout of a cell's ability to respond to optimum concentrations or combinations of detection agents (like and antibody or fluorescent dye) or modulation agents, such as a plasmid or siRNA liposome. The apparatus can also be used for cell-based screening of responses, including for example drug screening for different diseases or conditions (such as cardiac diseases, cancer, neurodegenerative disease), drug formulation design, patient-specific medicine (genetic medicine), or the like. It will therefore be appreciated that the response can include any response to conditions, although the apparatus is particularly suited to modulation of any activity of the cell.

It will be appreciated from the above, that the fluids can contain a wide range of agents, depending on the response to be induced. In the event that cell activity is to be modulated, the agent can be any suitable agent to which cells will react, such as a signalling agent, including hormones, growth factors, clotting factors, signalling molecules, promoters, inhibitors, or the like. However, it will be appreciated that any agent that has an impact on cell response can be used, including pharmaceuticals, or the like. Furthermore, fluids can contain agents in any form, such as dissolved, suspended solid agents, or the like.

Modulating agents can be an antibody, cytokines, chemokines, ions such as calcium and potassium, a DNA molecule, a DNA construct, an RNA molecule, an RNA construct, a viral particle encoding a DNA or RNA sequence, a fusion protein, a plasmid, a cosmid, a bacterial artificial chromosome, a construct encoding a DNA or RNA sequence, a carbohydrate, a metabolite, a nanoparticle, a microparticle, a liposome, a micelle, a polymer, conditioned medium (medium taken from a separate cell culture), fractions purified from conditioned medium, a natural extract (such as a composition isolated from naturally occurring biological sources), a cell culture component or medium component, a cell or organism (i.e. a co-cultured cell type or pathogen).

At least one of the fluids can further include a detection agent, to assist in monitoring the response of the substance. This can include, for example, the use of detection reagents such as fluorescent dyes, or the like.

A specific example of cell modulation will now be described in more detail. In particular, in this example, cells are provided in the wells of the well array, typically using a seeding process, as will be described in more detail below. Following this, the one or more fluids are selectively supplied to a first end of each well channel so that supplied fluid flows along the well channel to a second end of the well channel in the flow direction, thereby exposing the cells to the fluids and any modulating agents contained therein (referred to as exogenous modulating agents). As the cells are exposed to the fluids, this will typically cause a response within the cells, which in turn, may lead to the creation of further modulating agents (referred to as endogenous modulating agents), for example through the secretion of modulating agents by the cells. At least some endogenous modulating agents produced in an upstream well are then transferred to a downstream well as a result of the fluid flow, thereby further modulating cell activity in the downstream well. It will however be appreciated from the previous description that the presence of fluid flow is not essential and endogenous modulating agents can be transferred between wells using other mechanisms, such as diffusion, or the like.

Thus, endogenous modulating agents such as signalling agents can be secreted in a well following exposure of the cells to the exogenous modulating agent in the one or more fluids. The endogenous modulating agents are transferred to an adjacent or downstream well, together with the exogenous modulating agents, so that the cells in the adjacent or downstream well are exposed to both the exogenous and endogenous modulating agents. So, for example, if cells in the well 131.1 are exposed to a growth factor A, the cells may secrete further growth factors X, which are in turn transferred to the downstream well 131.2, meaning the cells in the well 131.2 are exposed to the growth factors A and X. Accordingly, it will be appreciated that in this example, this allows paracrine effects to be induced between the cells in the wells of the well channel 131.

The ability to allow substances in one well to be influenced by the response of the substance in an adjacent well provides a powerful mechanism for allowing investigation of secondary effects. In the case of the substances being cells, this is particularly useful in understanding the influence of the local cellular microenvironment on cell activity.

Once activity has been modulated, testing can then be performed to determine the outcome of the process. For example, an assay can be performed using appropriate markers to identify changes in cell activity. Additionally and/or alternatively cells and other contents of the wells can be extracted for further analysis. This can be used for example to identify any endogenous modulating agents, thereby allowing the exact conditions that lead to certain cell activity to be identified. The above described apparatus therefore allows a range of different types of study of cell activity to be performed, and in particular, allows the responsiveness of cells to specific modulating agents to be identified.

In the example of FIG. 1A, a number of channels 120 are also provided for supplying the respective fluids from the inlets 111, 112 to the well channels 131, 132, 133. In this example, a channel 121 extends from the inlet 111 to the well channel 131, whilst a channel 122 extends from the inlet 112 to the well channel 133. The channels 121, 122 also divide and combine to form a third channel 123 extending to the well channel 132. Each channel 120 has a respective channel geometry to thereby control a relative flow of fluids so that respective proportions of the fluids are supplied to each well channel 131, 132, 133.

Thus, as will be appreciated from the above examples, the channels 120 extending from the inlets can divide, to supply fluid to at least two well channels, or can combine to supply a mixture of fluids to at least one well channel.

In the current example, if first and second fluids A, B are supplied via inlets 111, 112, well channel 131 receives the first fluid A, well channel 132 receives a mixture of first and second fluids A and B, whilst well channel 133 receives the second fluid B only. In one particular example, the first fluid includes a factor and the second fluid includes a buffer so that different well channels 131, 132, 133 receive different concentrations of the factor.

It will be appreciated that the above arrangement therefore allows different fluids to be supplied to each well channel 131, 132, 133, so that the impact of different fluid combinations can be studied by comparing cell activity in the wells of each well channel. Accordingly, this allows a multi-dimensional study to be performed, with different wells channels receiving different fluids, and hence different combinations of exogenous modulating agents, and downstream wells of each well channel being further exposed to different endogenous modulating agents produced in upstream wells.

However, it will be appreciated that this is not essential, and as mentioned above, alternatively each well channel can receive the same fluids. In this instance, multi-dimensional analysis can still be performed, for example by inducing differences in environmental conditions between the well channels using other mechanisms, such as by selectively coating wells of different well channels with different coatings, or the like. Different well channels may also be exposed to different ambient conditions, such as different temperatures, levels of radiation, or the like.

In any event, it will be appreciated that the above described apparatus allows a wide range of different environments to be generated and the impact of these on cell activity easily compared.

Further features of the above described apparatus will now be described.

In one example, the flow of fluid along the channels can be controlled by altering any one or more aspects of the channel geometry including a channel shape, channel tortuousity, a channel length, a channel height, a channel width, and a channel angle. Additionally, further control can be provided by the inclusion of obstructions within the channel, such as pillars, staggered herring-bone mixers, multilayered passageways, or the like.

Thus, when substances are to be exposed, the relative proportions of different fluids that are supplied to the wells are determined, with the channel geometry being selected accordingly. This allows the channel geometry of each channel to be arranged so that each well channel receives an equal volume, flow rate, or volume per time, of fluid. This can help ensure the correct proportions of different fluids are supplied to the correct well channels in accordance with the channel configuration.

Further control can be implemented through the use of control devices, such as control valves, which can be provided in the channels 120, or the well channels 131, 132, 133, allowing fluid flow to different wells to be selectively restricted and/or stopped as desired.

The flow of fluid along the channels 120 and well channels 131, 132, 133 may also depend on properties of the fluid including the fluid viscosity, density, and surface tension.

The channels are typically microfluidic channels, and typically have a width of 1 mm or less or 0.25 mm or less, although any suitable channel size can be used.

Figure 1B:
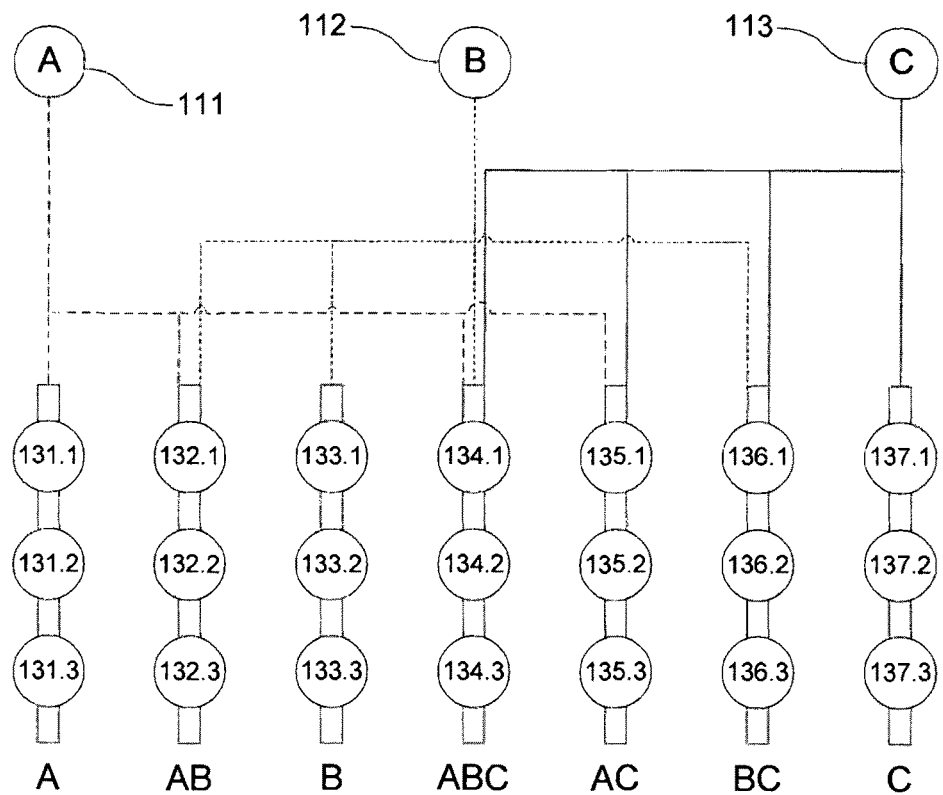

A range of different arrangements of inlets, wells and channels configurations can be used to provide a variety of exogenous modulating agents to the well channels. In the example of FIG. 1B, three inlets 111, 112, 113 are provided for receiving fluids A, B, C respectively. In this example, the inlets are connected via channels 120 to seven well channels 131, 132, . . . 137, with inlet 111 being in fluid communication with well channels 131, 132, 134, 135, inlet 112 being in fluid communication with well channels 132, 133, 134, 136, and inlet 113 being in fluid communication with well channels 134, 135, 136, 137. As a result, well channels 131, 132, 133, 134, 135, 136, 137 receive combinations of fluids A, A+B, B, A+B+C, A+C, B+C and C, respectively.

In the example of FIG. 1C, four inlets 111, 112, 113, 114 are provided. In this example, the inlets are provided in two inlet sets, with fluids A, B from the inlets 111, 112 being mixed to provide three fluid mixtures via the channels 121, 122, 123, and fluids C, D from the inlets 113, 114 being mixed and provided via the channels 124, 125, 126. The mixtures are supplied to the well channels 131, 132, 133, 134, 135, 136, 137, 138, 139. As a result, well channels 131, 132, 133, 134, 135, 136, 137, 138, 139 receive fluid combinations A+C, A+B, B+C, A+C+D, A+B+C+D, B+C+D, A+D, A+B+D, B+D, respectively.

In one example, each inlet set A, B; C, D receives a fluid including a respective factor and a separate buffer fluid, allowing different concentrations of different factors to be supplied to the well channels. For example, the fluids A, B correspond to a first factor and a buffer, whilst the fluids C, D correspond to a second factor and buffer. This arrangement therefore allows different concentrations of the first and second factors A, C to be supplied to each of the nine well channels 131, 132, . . . 139. In particular, the apparatus can generate all combinations of 3 concentrations each of the two factors A, C, thereby providing a full-factorial array having $3^2=9$ distinct conditions in total.

It should be noted that in the examples of FIGS. 1B and 1C separate channels are shown entering the well channels. However, this is for the purpose of clarity only, and more typically the channels will combine upstream of the well channel so that the fluids thoroughly mix before entering the well channels.

In the example of FIGS. 2A and 2B the apparatus of FIG. 1A is modified, with the modified apparatus 200 including mixing portions 221, 222, 223 provided in the channels 121, 122, 123, for mixing fluids contained therein. The mixing portion can be formed in any appropriate manner and can include the use of turbulators, advective or convective elements, or the like. Typically however, the mixing portions are formed from a tortuous portion of the channel, as shown in FIG. 2B. As also shown in FIG. 2A, the mixing portion is positioned downstream of the points at which any of the channels combine, thereby ensuring that different fluids are suitably mixed when supplied to the well channels. This helps ensure even exposure of substances in the well to the different fluids, and in particular to any agents contained therein.

A further example of apparatus will now be described with reference to FIGS. 3A to 3D. The following description will focus on the modulation of cell activity, but it will be appreciated that this is for ease of description only and that in practice techniques could be applied to a range of different substances and responses.

Figure 3A:
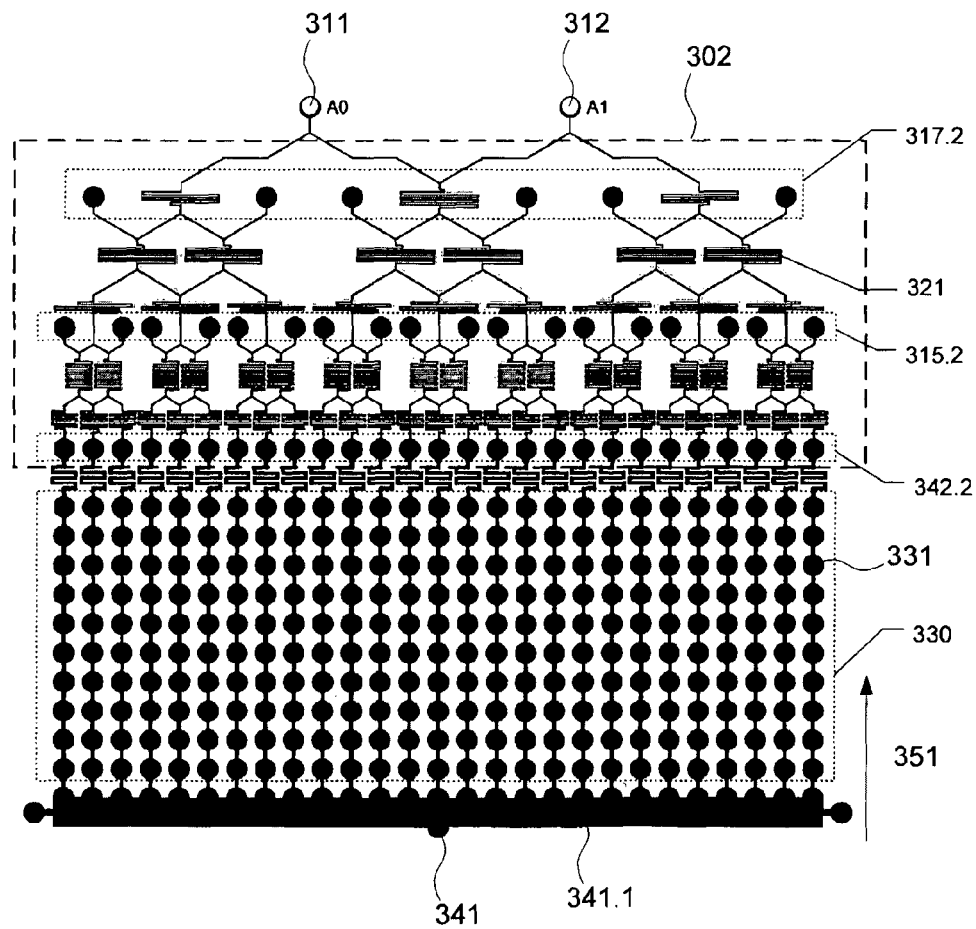
FIGS. 3A to 3C are schematic diagrams of a specific example of apparatus for modulating cell activity.
Figure 3B:
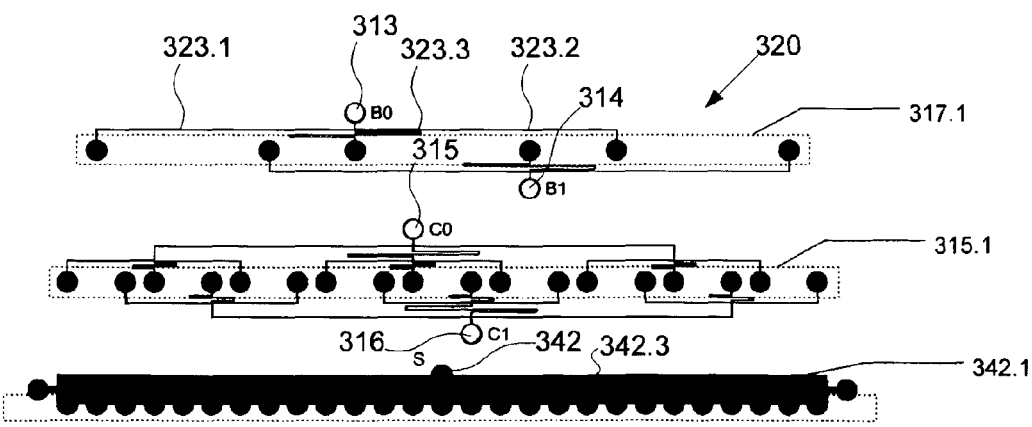
Figure 3C:
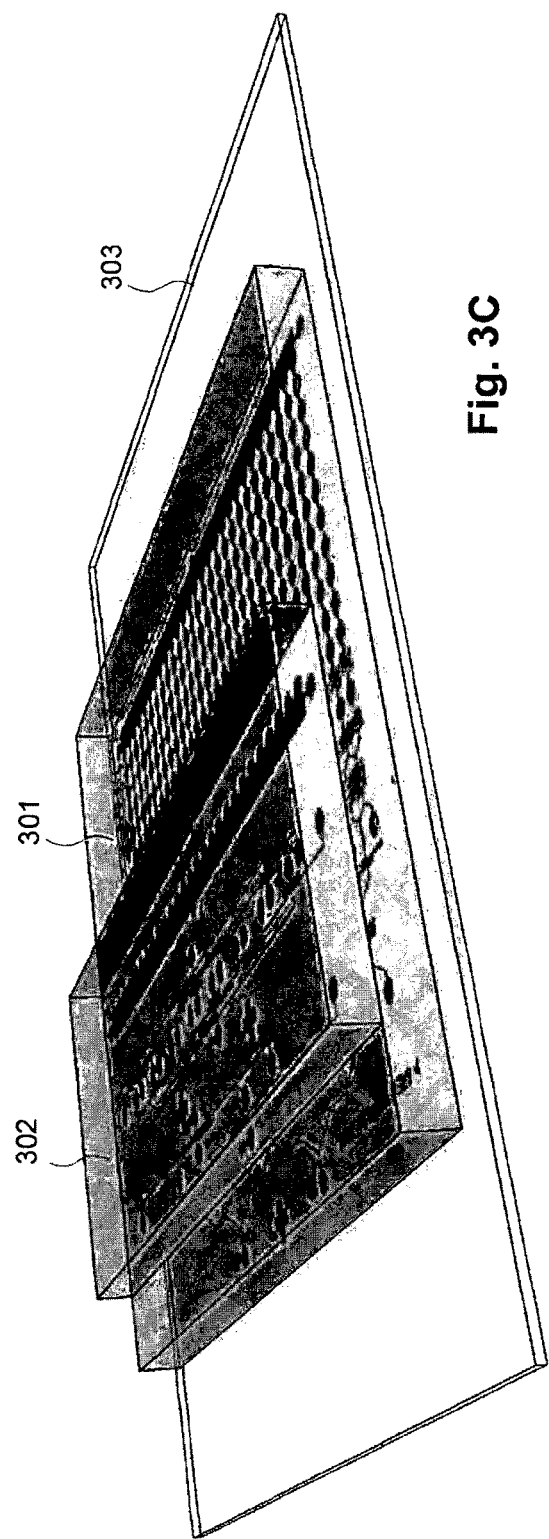

In this example, the apparatus 300 includes first and second cover layers 301, 302, mounted to a substrate 303, as shown in FIG. 3C. The first and second cover layers 301, 302 are typically formed from a polymeric material, such as poly(dimethylsiloxane) (PDMS), moulded so as to define the inlets, channels and the well array.

The configuration of channels and ports for the first and second layers are shown in FIGS. 3A and 3B respectively, with the second layer relative to the first layer 301 being shown in dotted lines in FIG. 3A. The layers 301, 302 are typically bonded to each other and to the substrate 303, which is typically made of an inert material, such as glass or the like, using a suitable bonding process such as adhesive or thermal bonding. However, other coupling techniques such as magnetic coupling, plasma coupling, covalent/chemical coupling, electrostatic coupling, mechanical coupling or the like, may be used. Materials may also be treated as required to make them suitable for use in the device, so that, for example, PDMS may be treated to avoid/reduce small molecule uptake.

It will be appreciated that other materials can be used for manufacturing the device, although in general materials should be biologically inert to prevent their interference with the cell modulation process. Additionally, in one particular example, materials are preferably optically transparent to allow the results of cell modulation to be easily identified, for example through the use of an appropriate assay. Additionally, the use of materials such as PDMS for the cover layers is particularly beneficial as this allows contents of the wells to be easily extracted from the apparatus, for example using a needle and syringe, or the like.

In this example, the apparatus 300 includes three sets of inlets 311, 312; 313, 314; 315, 316. The inlets are interconnected via channels 320 to the well array 330, which includes twenty seven well channels, each including ten wells, thereby defining a well array with two hundred and seventy wells.

As shown in this example, the inlets 313, 314, 315, 316 are provided in the second layer 302, with the inlets 311, 312 provided in the first layer 301. In use, each inlet 313, 314 is connected to three respective ports 317.1 via channels 323. When the second layer 302 is positioned relative to the first layer 301 as shown, the ports 317.1 align with corresponding ports 317.2 in the first layer 301, thereby supplying fluids from the inlets 113, 114. A similar arrangement is used with eighteen ports 318.1, 318.2 associated with the inlets 315, 316.

It will be noted that in this example, the channels 323.1, 323.2, 323.3, which couple the inlet 313 to the ports 317.1 are all of the same length. To achieve this, the channel 323.2 includes a tortuous section to maintain a given channel length. This is performed to maintain equal flow resistance along each of the channels 323.1, 323.2, 323.3, thereby maintaining equal flow of fluid along these channels.

As also shown, multiple mixing portions 321 are provided in the channels 320, thereby ensuring suitable mixing of the fluids contained therein.

In use, the first inlet set 311, 312 receives a first factor and a buffer, the second inlet set 313, 314 receives a second factor and a buffer and the third inlet set 315, 316 receives a third factor and a buffer. This allows respective combinations of first, second and third factors to be supplied to each of the twenty seven well channels, so that each well channel receives a respective concentration of each of the first, second and third factors, as will be described in more detail below.

In addition, the apparatus further includes a seeding inlet 341, which can be used for receiving a seeding fluid containing the cells. The seeding inlet is in fluid communication with the well channels via a seeding channel 341.1, which is typically connected to an end of the well channels opposite to the connection point for the channels 320. It will be appreciated that this allows the seeding inlet to also function as an outlet, allowing fluid that has flowed though the well channels to be expelled as required.

A seeding outlet 342 may also be provided. In this example, the seeding outlet 342 is provided in the second layer 302 in fluid communication with seeding ports 342.1 via a seeding channel 342.3. The seeding ports 342.1 are in fluid communication with corresponding seeding ports 324.2 in the first layer 301, which are in turn in fluid communication with the channels 320, as shown.

In use, a seeding fluid can be supplied to the well channels via the seeding inlet 341. The seeding fluid passes along the well channels in the direction of arrow 351, seeding the wells with cells. The seeding fluid then passes through the seeding ports 342.2, 342.1 and exits via the seeding outlet 342. Typically seeding fluid is passed through the wells for a period of time to ensure adequate population of the wells with cells.

In addition, the wells may be coated prior to introduction of the cells. The wells can be coated to assist with retaining cells within the wells, maintaining cell viability, or the like. The wells can be coated with any of the modulating agents or detection reagents, such as fluorescent dyes, or the like. Additionally, or alternatively this can be used to introduce markers for example for use in an assay, or the like. It will therefore be appreciated that coatings can include any suitable material, such as proteins, ligands, antibodies, nano- or micro-particles, conditioned media, fractions purified from conditioned media, natural extracts, such as a composition isolated from naturally occurring biological sources, RNA molecules or constructs, fusion proteins, cell culture components or medium components, carbohydrates or metabolites, viral particles encoding an exogenous DNA or RNA sequence, plasmid/cosmid/bacterial artificial chromosomes or other construct encoding an exogenous DNA or RNA sequence, cells or organisms (i.e. a co-cultured cell types or pathogens), or the like.

Such coatings can be applied either during manufacture or assembly of the apparatus, or alternatively, by passing a coating fluid through the well array 330. This can be achieved using the seeding inlet and outlet 341, 342, prior to seeding with cells, so that each of the wells receives the same coating. Alternatively, different coatings could be introduced via the inlets 311, 312, 313, 314, 315, 316, allowing different combinations of coatings to be supplied to each well channel, thereby allowing the impact of different coatings to be assessed. Furthermore, coatings may be applied during manufacture or prior to assembly of the device, by selectively processing any layer(s) of the device. This processing may include a process, such as dip-coating, spin-coating, lithography, etching, spotting, deposition, or other suitable process to introduce any of the coatings referred to previously or to modify any of the device substrates. The device can then be assembled as shown in FIG. 3C, for example, after this processing.

Once seeding of the wells is complete, the seeding outlet 342 can be blocked, for example using a stopper, or the like, so that when fluids are supplied via the inlets 311, 312, 313, 314, 315, 316, the fluids pass into the well channels, with the seeding inlet 341 acting as an outlet for fluid in the channels.

It will be appreciated that the particular seeding inlet and outlet arrangement is for the purpose of example only, and that in practice alternative configurations can be used. For example, if a seeding outlet is provided in the example of FIG. 1A, the seeding outlet could be provided in fluid communication with the channels 121, 122, 123.

It will be appreciated that the above described arrangements are for the purpose of example only, and that in practice a number of further variations are possible.

Figure 3D:
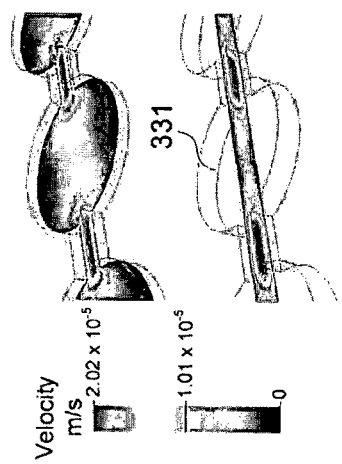
FIG. 3D is a schematic diagram showing the velocity of fluid flow through the wells of FIG. 3B.
Figure 3E:
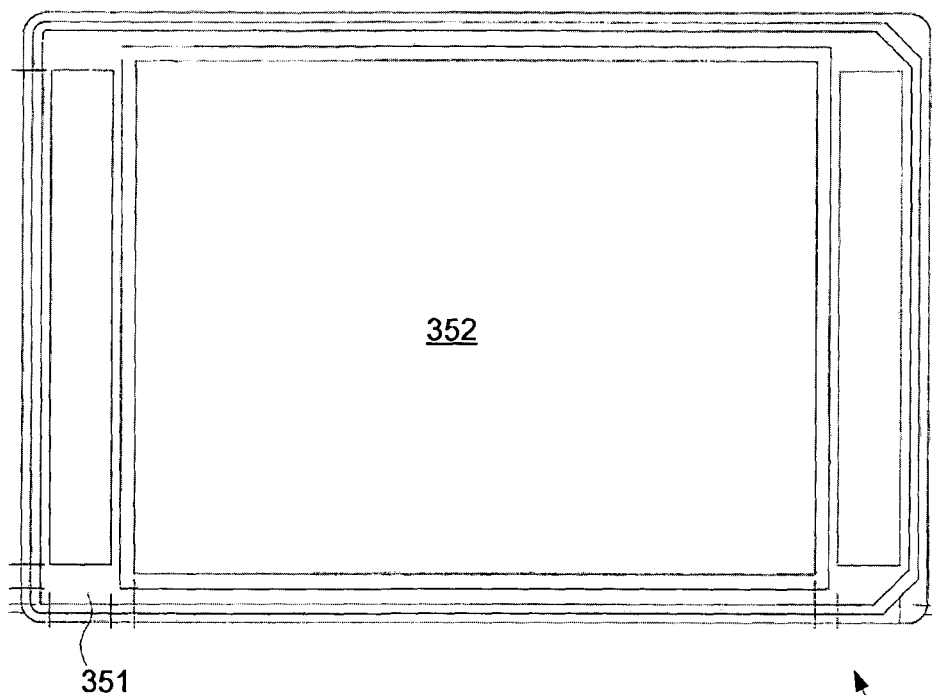
FIGS. 3E and 3F are schematic plan and side views of a holder for use with the apparatus of FIGS. 3A to 3C.
Figure 3F:
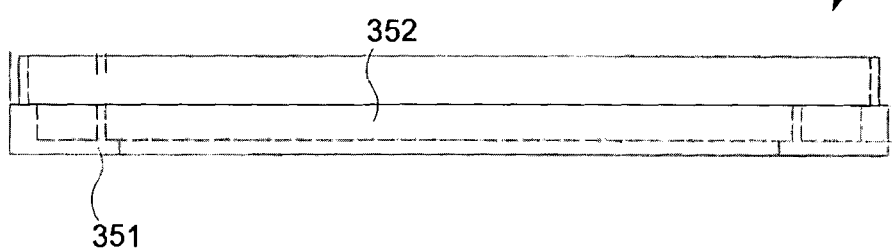

For example, the particular configuration of inlets and outlets, and in particular the position of these could be adjusted as required. This could be performed to allow the apparatus to conform to a standard architecture, for example to interface with existing fluid supply systems. This allows the apparatus to be provided as a stand alone device, which can then be used with existing hardware, thereby reducing overall costs to users of the equipment. The apparatus could also be provided in a cartridge, within, a standard housing, or with any other form of standard connector, further assisting integration into existing hardware. This can include standard fluidic clip connections to thereby ease connection of external equipment. The apparatus could also be mounted in a slide holder so that the apparatus presents a standard microplate footprint, thereby further assisting use with other equipment. An example arrangement is shown in FIGS. 3E and 3F. In this example, the slide holder 350 includes a body 351 defining a well 352 for receiving the substrate 303.

The relative resistances of the different flow paths defined by the channels can be adjusted as required, for example to take into account the fluid supply system used, as well as to adjust relative fluid flow through the device.

Additional environmental control can be achieved using other techniques, such as a gas flow cover and hydration pools. This can include the use of an iso-osmotic bath layer, which could be built into the device, for example within the second layer shown in FIG. 3B, with supply being either perfused or static.

The apparatus can include a built in media collection offtake, allowing fluid and/or substances to be extracted from the device as required. This could include for example a separate layer that interfaces with the well array, allowing well contents to be selectively removed.

The apparatus can include additional control or sensing devices for ensuring consistent delivery of fluid across the well array, such as a bubble trap, gas exchanger, bubble-sensing electrode or sensor, or the like.

In use, a priming step may be performed, such as flushing the apparatus with a medium to equilibrate conditions across the well array.

Control devices can be in-built into the channels and/or well channels to further control fluid flow. This can include the use of diffusion barriers to limit diffusion of agents between wells, thereby allowing for flow to be stopped for prolonged periods without unwanted diffusion of agent between wells. This can also be achieved through the use of increased length of resistance sections, as well as increasing the separation between wells on a well channel. Additionally, valves can be used to isolate individual wells, as well as to provide for extraction of fluid from individual wells. An equal-resistance (fractal) outlet channel section can also be provided to improve flowrate distribution.

Other control devices that can be used include the use of plug and inlet clips for selectively closing inlets and/or channels, thereby allowing the device to switch between different modes, such as an exposure mode and a seeding mode. This can also be used to seal the device, for example to contain waste products, post use, as well as to allow pressure within the wells and channels to be controlled. Such plugs could also be provided in a comb arrangement allowing multiple channels to be blocked simultaneously.

A range of different detection mechanisms can be used to determine the response of substances. A separate fluidics arrangement may be provided extending from readout/visualization area and mask with a cover can be used. This allows the well channels to be exposed, whilst the remaining channels are covered by an opaque layer, so that they are not visible. This can be useful when automated sensing arrangements are used to detect substances in the wells by preventing unwanted signals arising from substances in the channels 320 and seeding channel 341.1.

An SBS microtiter plate can be used for offtake of any one or more of fluid medium, cells, lysates, substance or the like. In one example, this can include a plug which interfaces to 1,536 well plate.

It is also possible to provide individual column or well fixates or lysates (RLT, RIPA, etc.). The device may also include the ability to retrieve cells from individual wells or subsets of wells, in a range of formats or buffers, including intact live cells, fixed (for example, with paraformaldehyde or a suitable fixative) samples of cells, cell lysates, or RNA isolation preparations, for example.

Operation of a specific example of the apparatus 300 will now be described in more detail with respect to example experiments.

In these examples, the apparatus was designed using scalable, hierarchically-nested dilution networks and resistive flow principles, fabricated to 250 µm channel height by SU-8 2100 photolithography and poly(dimethylsiloxane) (PDMS) soft lithography molding, and assembled by bonding the first and second layers 301, 302 and the substrate 303, in the configuration shown in FIG. 3C.

The full-factorial multiplexing of exogenous factors is encoded solely by the arrangement of the inlets 311, 312, 313, 314, 315, 316 and the channels 320, and does not rely on integrated valves or extensive peripheral connections.

It will be appreciated that this allows the apparatus 300 to be readily scalable by adding parallel or serial replicate wells (linear scaling of experimental points), additional concentration levels (polynomial scaling) or additional factors (exponential scaling) with a zero, zero or linear increase in the number of fluidic connections, respectively, and no increase in physical layers.

The apparatus generates all combinations of 3 concentrations each of 3 soluble factors (a full-factorial array; $3^3=27$ distinct conditions in total, from only 6 fluidic inputs. Importantly, this flexible architecture is readily scalable to a parallel and/or serial replicate wells (linear scaling of experimental points), b concentration levels (polynomial scaling), and c exogenous factors (exponential scaling), giving a total of $ab^c$ experimental points.

After diffusive mixing, the array supplies exogenous factors to the well array 330, which as described above includes 270 wells, acting as culture wells, and which are sized and arranged similarly to a 1536-well microtiter plate. The grid comprises 27 columns of 10 serial culture wells—each column constitutes a distinct composition of exogenous factors, whereas endogenous paracrine factors are progressively accumulated during continuous fluid flow along the well channel.

In this example, the well channel is 250 µm wide, with the wells 331 being 1.63 mm in diameter and 250 µm high. Under the nominal flow conditions for hESCs, computational fluid dynamic modelling shows cells in the culture wells are exposed to slow, creeping laminar flow and low resultant shear stresses, while 250 µm wide interconnects between wells 331 serve to spatially discretise the wells 331, as shown in FIG. 3D. These flow characteristics ensure that modulating agents can be transferred between wells, whilst ensuring that the cells undergo minimal disruption from the fluid flow.

Dye Loading

Figure 4A:
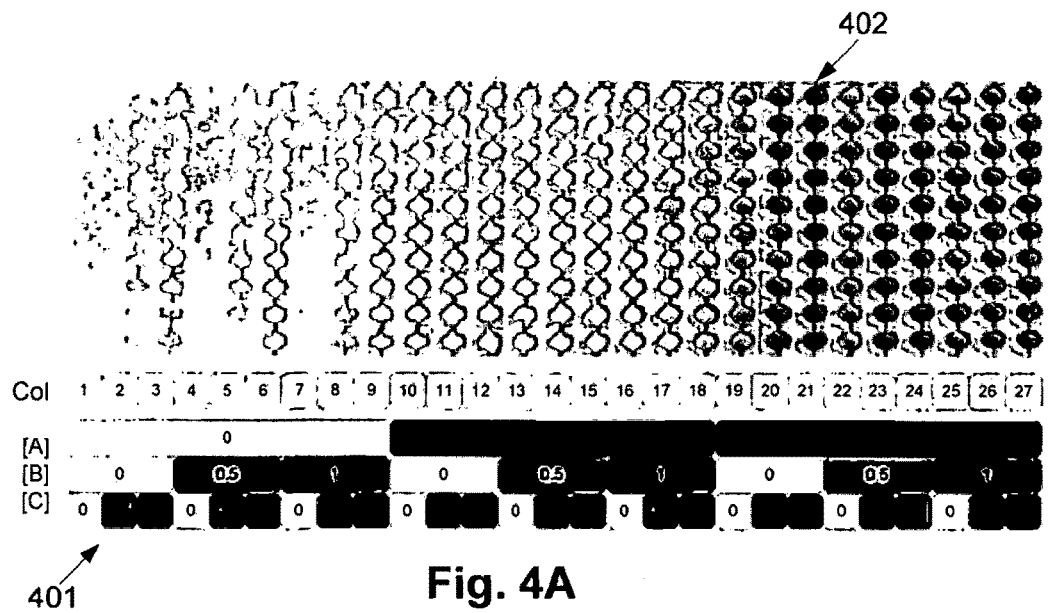
FIG. 4A is a diagram showing an example of the relative concentrations of dyes in the wells of FIG. 3B.

To evaluate the spectrum of soluble conditions formed by the array, dye-loading experiments were performed, with fluorimetric quantification being used to determine the soluble factor levels in each of the wells. In this example, red, yellow and blue dyes are used to simulate factors A, B, C being provided to the inlets 312, 314, 316. PBS fluid is supplied to the inlets 311, 313, 315 thereby simulating mixing of three factors and corresponding buffers. Stock solutions are provided at a normalised concentration of 3 to allow for subsequent dilution. The theoretical concentrations of each of the factors A, B, C are shown in the panel 401, with a photograph of the resulting dye distribution being shown in panel 402, of FIG. 4A.

Figure 4B:
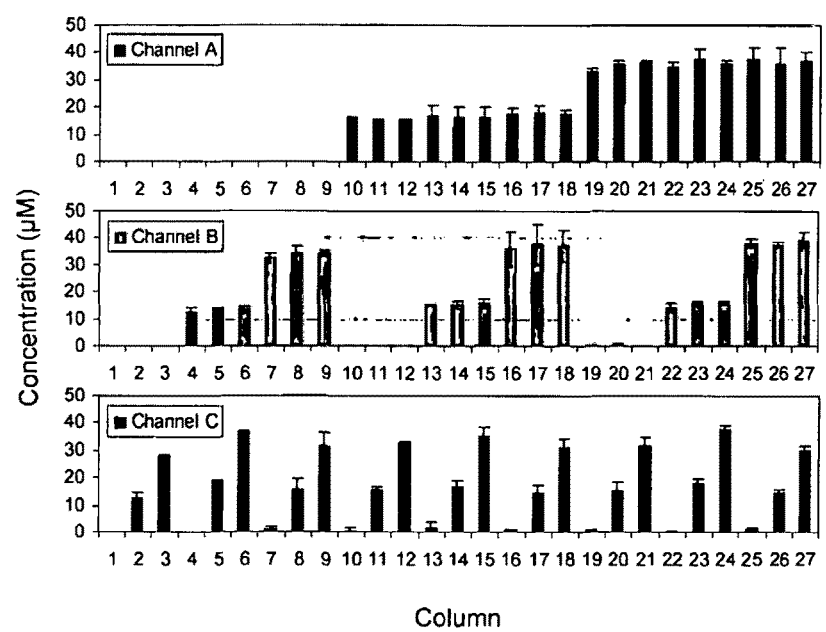
FIG. 4B is a graph showing the measured concentration of dyes in the wells of FIG. 3B.

Fluorimetric quantification of soluble factor levels in each column in the array (i.e. along each well channel) was performed. Factor channels A, B and C were quantified serially and independently, with the results being shown in FIG. 4B. Detection of fluorescence in zero-concentration conditions in Channels B and C is due to residual, adsorbed dye. Bars represent mean+/−S.D. of 2 independent experiments. The results confirm the generation of a full-factorial spectrum of conditions across the well array, as well as adequate diffusive mixing of factors up to 40 kDa. The accurate generation of all concentration levels also implied that the flow distribution through the device was in agreement with design flowrates and equal between columns.

A number of experiments were performed using the HES3-EOS-C(3+)-EiP Pluripotency Reporter hESC Line. The experimental procedures used will now be summarised, with the results for a number of experiments being described below.

HES3-EOS-C(3+)-EiP Pluripotency Reporter hESC Line

The PL-SIN-EOS-C(3+)-EiP (Addgene plasmid 21313) lentiviral reporter construct expresses eGFP-IRES-puromycin-N-acetyltransferase under the control of a chimaeric promoter, comprised of the mouse early transposon (ETn) promoter and 3 Oct4/Sox2 binding motifs derived from the distal enhancer (conserved region 4) of the Oct4 (also, Pou5f1) gene, which is highly active specifically in pluripotent cells. Lentiviral and packaging vectors were transfected into 293FT cells for viral particle production. HES3 hESCs adapted to single-cell passaging were transduced with lentiviral particles and maintained in mTeSR-1/Matrigel cultures under selection in the presence of 2-2.5 µg/mL puromycin.

Array Screening and Static Controls

The apparatus 300 was autoclaved, filled according to the "channel-outgas technique", then surface-coated (2-4 h, room temperature) with a single injection of either 400 µg/mL (total of 10 µg/cm$^2$ protein supplied) purified human fibronectin (BD Biosciences, North Ryde, Australia) (HES3-EOS-C(3+)-EiP experiments), or a limiting dilution of hESC-qualified Matrigel (BD Biosciences) (HES3-MIXL-GFP experiments) identified through attachment assays.

hESCs maintained in tissue culture flasks were detached with TrypLE Express, triturated to approach a single-cell suspension then washed with and resuspended in mTeSR-1 at 1.6×10$^6$ cells/mL (HES3-EOS-C(3+)-EiP experiments, 4×10$^4$ cells/cm$^2$ surface density) with inclusion of 10 µM ROCK inhibitor (Y-27632 dihydrochloride monohydrate, Sigma-Aldrich, Australia), or at 3.0×10$^6$ cells/mL without ROCK inhibitor (HES3-MIXL-GFP experiments, 7.5×10$^4$ cells/cm$^2$).

Cells were allowed to attach to the well array 330 for 8-10 h in an incubator (37° C., 5% CO2 in air), then subjected to continuous fluid flow under the specified factor conditions at 60 µL/h total flowrate.

Positive-displacement-driven flow was provided by a syringe pump (NE-1800, New Era Pump Systems), via 3 or 1 mL syringes (Terumo, Somerset, N.J.), and polyethylene tubing (PESO, 0.58 mm ID, BD, North Ryde, Australia), with stainless steel, 22 gauge blunt-nose needle tips as connectors to the inlets. All media were further supplemented with 1% v/v penicillin/streptomycin solution. Static culture controls in 24-well plates were coated at solution concentrations adjusted to give equivalent total amounts of protein supplied per surface area, and were also seeded with equivalent surface densities of cells, with media Changed daily until the experiment endpoint (see also Supplementary Methods).

For use in apparatus 300, conditioned medium was recovered from static controls differentiated in 10 ng/mL BMP-4 and 6 ng/mL Activin A in RPMI B27 medium. Cells were removed by centrifugation and supernatant medium stored at 4° C. Media from days 1 and 2 were mixed and BMP-4 and Activin A re-supplemented at 50% of nominal levels before use in arrays.

In Situ Immunofluorescence Staining and Confocal Imaging

Incubation is terminated at 6.5 d (HES3-EOS-C(3+)-EiP experiments) or 2.5 d (HES3-MIXL-GFP experiments) after the start of fluid flow for in situ immunostaining. When performing the experiments, the inlets 311, 312, 313, 314, 315, 316 were initially plugged closed and the common seeding/coating outlet 342 left open. Serial exchange of staining and washing solutions was driven by a syringe pump.

The well array 330 was washed with PBS and fixed with 2% paraformaldehyde/PBS solution (30 min, RT), followed by blocking with 3% bovine serum albumin (BSA)/PBS solution with 0.2% sodium azide (30-45 min, RT). Markers were detected with primary antibodies against TG30 (4 µg/mL, Ms IgG2a isotype, Millipore) and TRA-1-60 (4 µg/mL, Ms IgM isotype, Millipore) in 0.3% BSA/PBS (1 h, RT).

The well array 330 was then washed with 0.3% BSA/PBS and subsequently treated with a solution of isotype-matched secondary antibodies (Goat anti-Ms IgG (H+L)-Alexa Fluor 568, Goat anti-Ms IgM-Alexa Fluor 647, both 4 µg/mL, Molecular Probes, Eugene, Oreg.) and 10 µg/mL Hoechst 33342 (Molecular Probes) in 0.3% BSA/PBS (1 h, RT). HES3-MIXL-GFP arrays were stained only with Hoechst.

The well array 330 is then washed/mounted in 0.3% BSA/PBS for imaging 16-bit, multi-colour tile scan montage images of entire apparatus 300 comprising 270 culture wells were acquired with a Zeiss LSM 710 laser scanning confocal microscope system and Zen 2008 acquisition software (Carl Zeiss, North Ryde, Australia). To adjust for intensity variations due to sample tilt and to completely capture nuclear and membranous staining which varied in intensity in the z-direction, optical sections were acquired and then processed into a maximum intensity projection, which was used for image analysis.

Data Processing and Statistical Methods

Total fluorescence intensities ($T_{EOS\text{-}GFP}$, for example) were extracted from arrays with AGScan (https://mulcyber.toulouse.inra.fr/projects/agscan/). Spot intensities in each channel were linearly transformed about the mean and standard deviation for all spots in that channel in an individual array, by $I_{EOS\text{-}GFP} = (T_{EOS\text{-}GFP} - \mu_{EOS\text{-}GFP})/\sigma_{EOS\text{-}GFP}$, where $I_{EOS\text{-}GFP}$ is the expression index of EOS-GFP, and $\mu_{EOS\text{-}GFP}$ is the mean and $\sigma_{EOS\text{-}GFP}$ the standard deviation of all $T_{EOS\text{-}GFP}$ for a particular array. This provides expression indices ($I_{EOS\text{-}GFP}$, $I_{MIXL1\text{-}GFP}$) rating each spot's intensity in terms of global standard deviations relative to the global mean.

Factorial analyses are performed on expression index data with MINITAB 15 software (Minitab Inc.). Expression indices were designated as response variables and soluble factors designated as inputs. A fourth input variable, 'Position', was defined based on each culture well's row coordinate in the array. Effect magnitudes were then generated by MINITAB according to methods described elsewhere[45]. Pearson product-moment correlation coefficients ($r_{X,Y}$), coefficients of determination for linear regression ($R^2$), and Student's t-test statistics were calculated with Microsoft Excel. For Student's t-tests, two-tailed tests were performed for two samples assuming unequal variances, and differences with $p<0.05$ were considered significant.

Primitive Streak Induction and Chemical Modulation

HES3-MIXL1-GFP hESCs maintained in mTeSR-1/Matrigel cultures were detached with TrypLE Express, seeded at $7.5 \times 10^4$ cells/cm$^2$ into 24-well plates coated with a limiting dilution of hESC-qualified Matrigel and allowed to attach overnight, after which cultures were typically ~60% confluent. MIXL1-GFP expression was then induced by differentiating in RPMI B27 medium with 10 ng/ml BMP-4 and 6 ng/ml Activin A (both R&D Systems) for 2.5 d with optional addition of 5 µM IWP-4 and 5 µM CHIR99021 (both Stemgent), or 0.1% v/v DMSO vehicle control.

The results of each experiment will now be described.

hESC Pluripotency Screening in a Microbioreactor Array

Figure 5A:
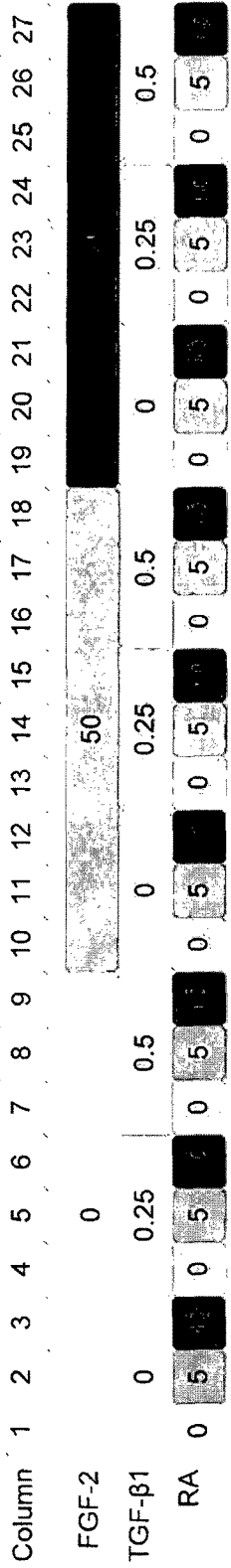
FIG. 5A is a diagram of an example of screening conditions used for pluripotency screening of HES3-EOS-C(3+)-EiP hESC using the apparatus of FIGS. 3A to 3C.

In order to validate the performance of the apparatus 300 in a biological screening process, pluripotency screening of HES3-EOS-C(3+)-EiP hESC under defined conditions was performed. For this experiment a background of custom mTeSR-1 medium (Cat#05892, StemCell Technologies, Vancouver, BC) minus the maintenance factors FGF-2 and TGF-β1, and an attachment substratum of purified human fibronectin (BD Biosciences, North Ryde, Australia). hESCs were cultured under constant flow (60 µL/h total) for 6.5 days in a full-factorial array of FGF-2, TGF-β1, and retinoic acid (RA). The screening conditions are shown in FIG. 5A, with the numbers indicating relative concentrations of FGF-2 (ng/mL), TGF-β1 (ng/mL), and RA (µM). Maintenance factors were titrated back into the media using the well array 330, and retinoic acid was included as an internal differentiation control.

GFP expression by a lentivirally-transduced pluripotency reporter line, HES3-EOS-C(3+)-EiP was used as a sensitive readout of pluripotency status. The utility of the pluripotency reporter line was validated and its sensitivity in response to various maintenance and differentiation stimuli were characterised in static controls (24-well plates) run in parallel with arrays. Pluripotency was further confirmed by in situ co-immunostaining for the surface markers TG30 and TRA-1-60 at the experiment endpoint, and DNA was counterstained with Hoechst 33342 (Supplementary Methods). The immunodetection phase did not noticeably affect cell numbers or GFP fluorescence in the array.

Figure 5F:
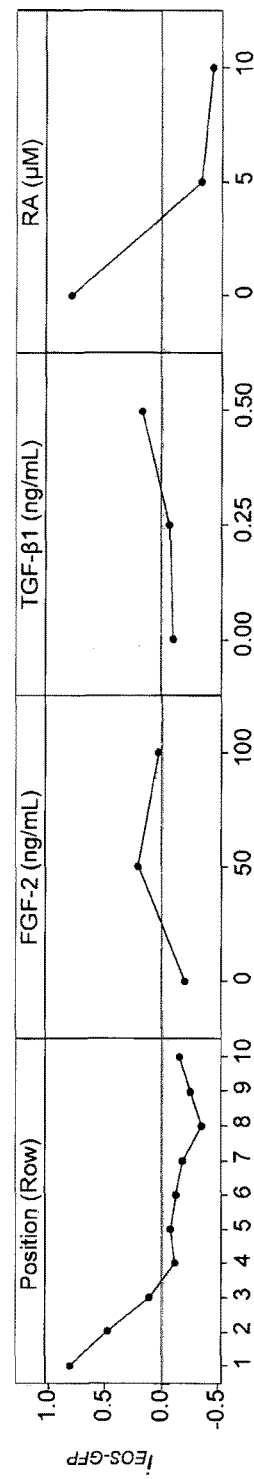
FIG. 5F shows graphs of example of the main effect magnitudes of factors on an expression index for the screening conditions of FIG. 5A.
Figure 5B:
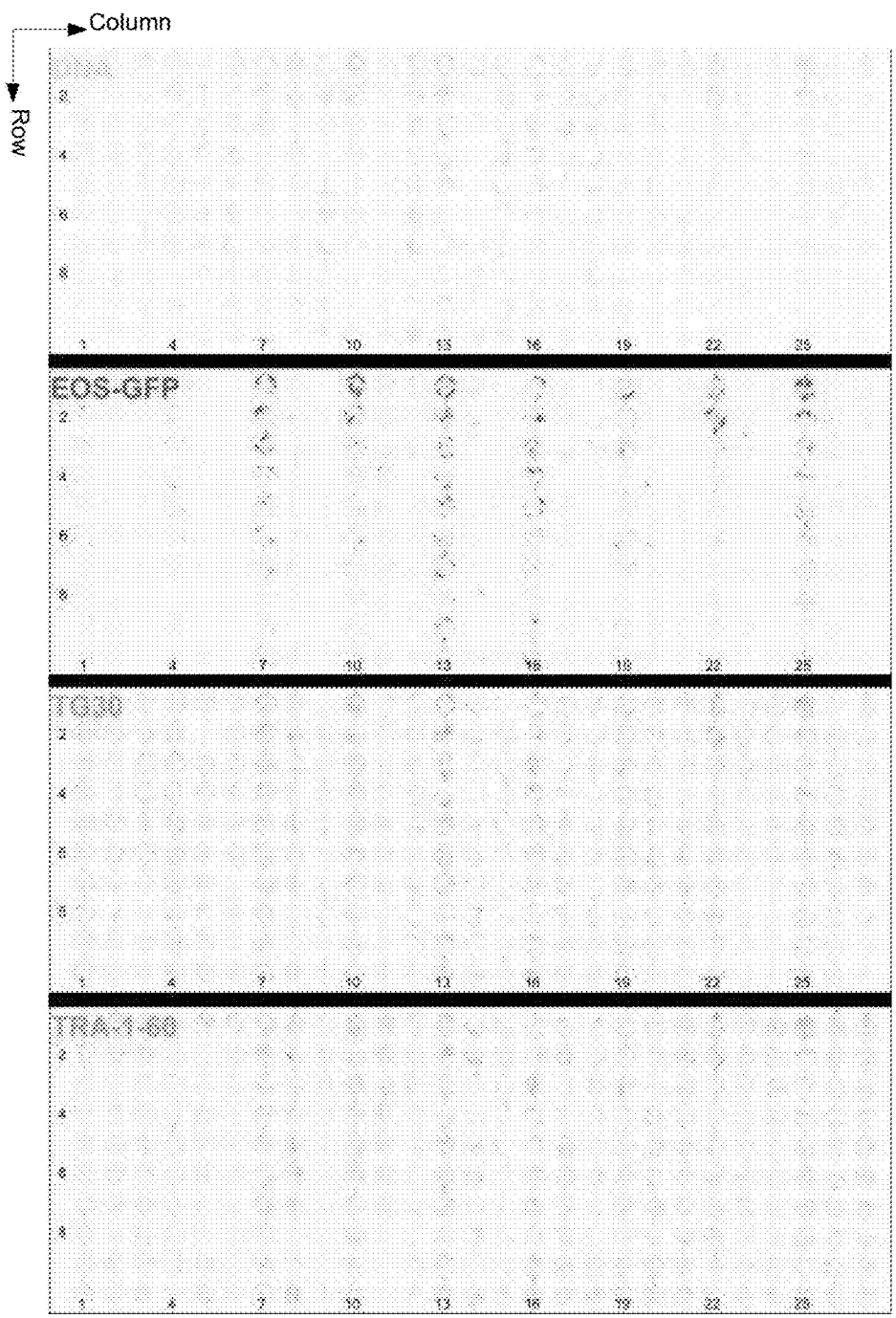
FIG. 5B is an example of a laser scanning confocal negative image for the screening conditions of FIG. 5A.
Figure 5C:
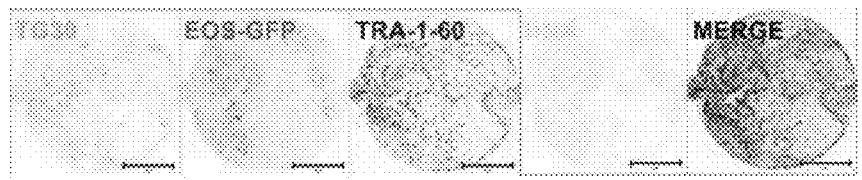
FIGS. 5C and 5D are examples of higher magnification laser scanning confocal negative image of selected wells for the screening conditions of FIG. 5A.
Figure 5D:
Figure 5E:
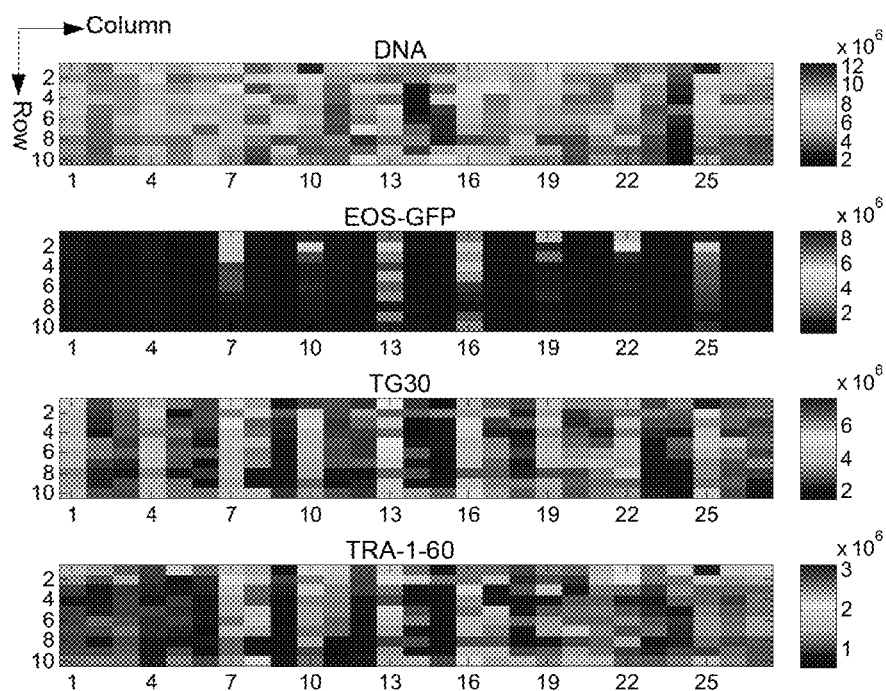
FIG. 5E shows example heatmaps of total fluorescence intensities in the well array for the screening conditions of FIG. 5A.

Multi-channel fluorescence data were captured by laser scanning confocal imaging, with the resultant images being shown in FIG. 5B. Higher-magnification images of wells from Row 1 of the array, for column 25, and column 3 are shown in FIGS. 5C and 5D, respectively. The scale bar corresponds to 500 Heatmaps of total fluorescence intensities in the array (arbitrary units) are shown in FIG. 5E. Spot intensities were linearly transformed about the mean and standard deviation for all spots in an individual array to provide expression indices (IEOS-GFP, for example). This approach is similar to measures taken for ECM arrays and has the effect of clearly highlighting "hits" in the screen, where a strong positive or negative effect is seen in one condition relative to the mean of all treatments. The global normalisation method does not allow direct comparison of absolute expression levels between different arrays or plate controls without additional calibrators.

The results show GFP expression in the HES3-EOS-C (3+)-EiP reporter line had a high dynamic range and strict response at 6.5 d, where treatment with 5 or 10 µM RA abrogated EOS-GFP expression to a low baseline level, regardless of FGF-2 or TGF-β1 treatment. Columns 1 (no factors) and 4 (0.25 ng/mL TGF-β1) also had similar EOS-GFP expression to RA-treated conditions, showing sensitivity to absent or insufficient pro-maintenance signals. TG30 and TRA-1-60 exhibited lower dynamic range than EOS-GFP, and had a more promiscuous distribution of expression throughout the array.

There was residual expression at 6.5 d in some RA-treated conditions, as shown in FIGS. 5E and 5F, which seemed to display more of an integrative effect with FGF-2 and/or TGF-β1 treatment. The highest response for all 3 pluripotency markers occurred at Column 25 in the first row, which corresponds to direct supply of reconstituted mTeSR-1 conditions. Hence, from a validation standpoint, the array was able to recapitulate the efficacy of mTeSR-1 medium, even under the imposed slow perfusion conditions.

It should be noted that the results highlight that pluripotency marker expression was position-dependent, and in particular varies along the length of a well channel, even though common factors are supplied to the well channel. In the current experiment, the highest expression of pluripotency markers occurred in the first row of the array, followed by decreasing gradients of expression through successive downstream wells. To extract such emergent signatures from the array, the positional coordinate (row number) of wells in a well channel were included as an input factor for factorial analysis to characterise putative paracrine effects, which are otherwise difficult to explicitly isolate in conventional culture formats. Factorial analysis then revealed the main effects of individual factors, as shown in FIG. 5F.

The peak EOS-GFP expression in the first row suggests the exogenous factors were able to act directly to maintain pluripotency. If generation of autogenic feeder cells or accumulation of paracrine factors were required, EOS-GFP expression would be predicted to reveal downstream maxima or increasing gradients. Since HES3-EOS-C(3+)-EiP cells were puromycin-selected for pluripotent cells prior to screening, it is unlikely such autogenic feeders were present in initial cultures. Results indicate that the decrease in GFP is as a result of the production of diffusible factors being transferred between wells.

It is not clear from the array data if there were significant differences in position-dependent expression resulting from addition of 0.25 or 0.5 ng/mL TGF-β1, however, columns devoid of TGF-β1 (Columns 10 and 19) also showed decreasing gradients, signifying the presence of a distinct effector. Moreover, influence from metabolites was considered. However, at row 10 and at maximal cell densities, glucose depletion is estimated at ~3 mM (22% of mTeSR-1 levels), and lactate accumulation at ~7 mM (32% of levels shown to partially reduce TRA-1-60 expression after 3 weeks[19]). The negative paracrine effect therefore appears to be caused by a complement of secreted factors that have a net pro-differentiation effect. This is in accord with detection of such factors in hESC-conditioned medium.

Normalisation of EOS-GFP data to DNA, ignoring all RA-containing conditions revealed a position-dependent effect. Pluripotency marker expression indices were strongly correlated, with correlation coefficients ($r_{X,Y}$) of $r_{EOS-GFP,TG30}=0.77$, $r_{EOS-GFP,TRA-1-60}=0.64$ and $r_{TG30,TRA-1-60}=0.75$, based on paired total intensities of all 270 spots. Replicate array experiments were also highly correlated, with $I_{EOS-GFP}$, $I_{TG30}$ and $I_{TRA-1-60}$ data having $r_{Array1,Array2}$=0.60, 0.64, and 0.41, respectively, based on paired total intensities of all 270 spots, or $r_{Array1,Array2}$=0.73, 0.86, and 0.44 for paired mean intensities from rows 1-5. This compares favourably to published ECM protein array experiments which had correlation coefficients of 0.35-0.65 for averaged responses taken from a subset of spots.

Primitive Streak Differentiation Screening hESC differentiation protocols typically rely on embryoid bodies (EBs) to drive the emergence of a target phenotype. However, EBs are heterogeneous, and contain unspecified spatial gradients of signalling activity, providing little control of paracrine signals. Differentiation outcomes have also been shown to be highly dependent on the size of EBs, implicating microenvironmental parameters resulting from localised cell density, such as paracrine factor accumulation, as being critically involved. While experiments utilising forced aggregation of reporter gene-marked mESCs have attempted to dissect this, such an approach masks internal spatio-temporal variations in microenvironmental composition within the embryoid bodies and makes it difficult to link defined combinations of stimuli to specific differentiation outcomes.

To further demonstrate the ability of the apparatus 300 to provide these faculties, hESCs were differentiated towards a primitive streak-like (mesendodermal) phenotype marked by the transcription factor MIXL1. HES3-MIXL1-GFP hESCs (also, HES3 MIXL1$^{GFP/w}$ hESCs; karyotying and in vivo teratomas) growing as a monolayer were differentiated under continual flow in the apparatus 300 for 2.5 d in a full-factorial array of BMP-4, Activin A, and the GSK-3β inhibitor/canonical Wnt activator 6-bromoindirubin-3'-oxime (BIO) in RPMI B27 medium. A screening panel showing array conditions is shown in FIG. 6A, with numbers indicating concentrations of BIO (μM), BMP-4 (ng/mL) and Activin A (ng/mL).

Figures 6A, 6E:
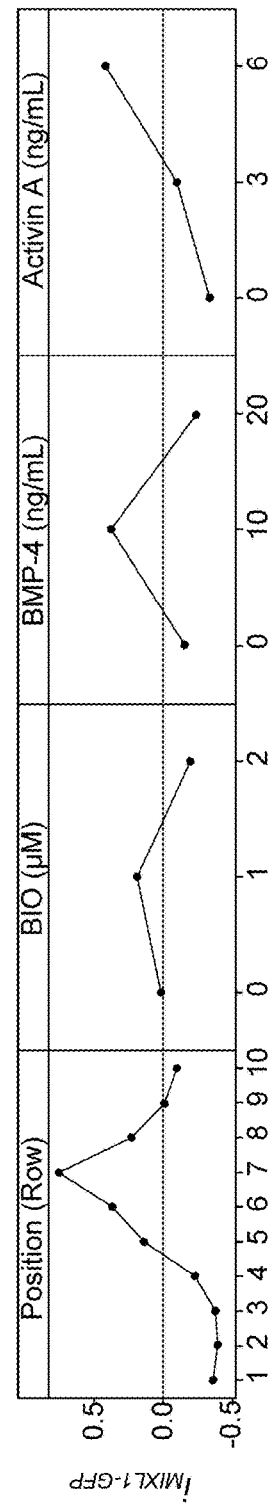
FIG. 6A is a diagram of an example of screening conditions used for screening of HES3-MIXL1-GFP cells for induction of primitive streak marker MIXL1 and modulation of paracrine effects, using the apparatus of FIGS. 3A to 3C.
FIG. 6E shows graphs of examples of the main effect magnitudes of factors on an expression index for the screening conditions of FIG. 6A.
Figure 6B:
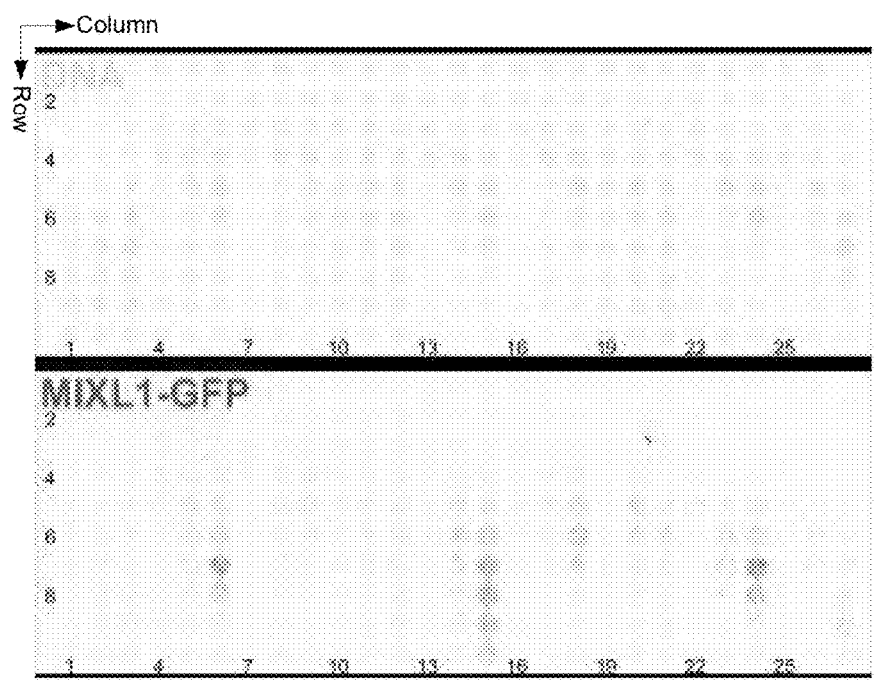
FIG. 6B is an example of a laser scanning confocal negative image of the well array for HES3-MIXL1-GFP hESCs expressing GFP and counterstained with Hoechst at experiment endpoint for the screening conditions of FIG. 6A.
Figure 6C:
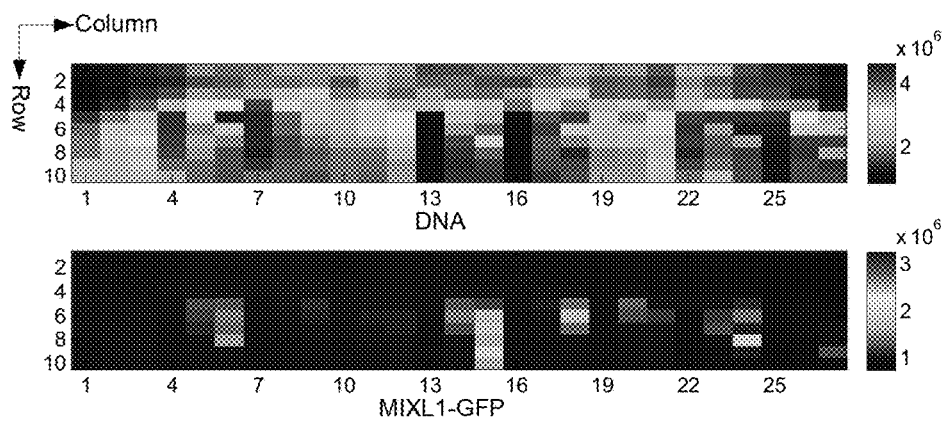
FIG. 6C shows example heatmaps of total fluorescence intensities in the array for the screening conditions of FIG. 6A.
Figure 6D:
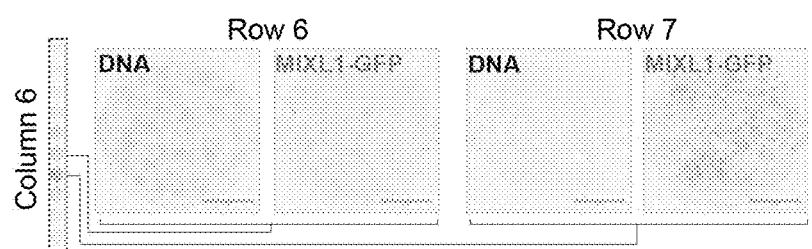
FIG. 6D are examples of higher-magnification confocal imaging of individual wells within the array for the screening conditions of FIG. 6A.

A confocal tile scan image of HES3-MIXL1-GFP hESCs expressing GFP and counterstained with Hoechst at experiment endpoint is shown in FIG. 6B, with heatmaps of total fluorescence intensities in the array being shown in FIG. 6C. Higher-magnification confocal images of individual wells within the well array 330 are shown in FIG. 6D, with the scale bar indicating a length of 500 μm.

Endpoint MIXL1-GFP expression was activated under tightly delineated factor conditions, with the highest expression in columns 6, 15 and 24—conditions which each contained 10 ng/mL BMP-4 and 6 ng/mL Activin A, combined with 0, 1 or 2 μM BIO, respectively, as shown in FIGS. 6B and 6C. Of note, high MIXL1-GFP-expressing wells, which contain cells characterised by dim Hoechst DNA staining were in each case immediately preceded by a "DNA-bright" well, characterised by clustered layers of cells and bright DNA staining. This periodic recurrence of phenotypes suggests discrete patterning of comparatively homogeneous intermediate populations in individual wells (i.e. in a tightly delineated set of conditions) resulting from unique and defined combinations of exogenous and paracrine factors. Replicate array experiments as in FIG. 6A had correlation coefficients of 0.66 and 0.69 for $I_{DNA}$ and $I_{MIXL1-GFP}$, respectively.

Factorial analysis for the expression index $I_{MIXL1-GFP}$, as shown in FIG. 6E, showed a linear, positive dependence on Activin A, optima for BIO and BMP-4 concentrations at 1 μM and 10 ng/mL, respectively. Factorial analysis also highlighted the synergistic action, of BMP-4 and Activin A when combined at optimal concentrations. Most notably though, the positional dependence exposed a "paracrine signature" with an optimum at row 7 which was preceded by an increasing exponential trend and immediately followed by a decreasing exponential trend in expression levels. Across the whole array, appreciable MIXL1-GFP expression was only detected below the 4th row of wells, suggesting that combinations of only BMP, Activin and canonical Wnt stimulation were not sufficient to directly activate MIXL1 expression. Arrays run for 3.5 d had a similar distribution of GFP expression, suggesting deficiencies in the initial rows were not purely due to insufficient induction time. Rather the progressive accumulation of paracrine soluble factors through a series of culture wells is required for MIXL1 activation.

In strong support of the existence of such transferable paracrine factors, MIXL1-GFP expression was observed to shift towards the top rows of the array in a dose-dependent manner when induction-conditioned medium (re-supplemented with 50% of nominal factor levels) was provided as a factor in subsequent experiments.

To demonstrate the capability for identification of factors responsible for this, the apparatus 300 was further used to screen FGF signalling as a candidate paracrine signal.

Figure 7A:
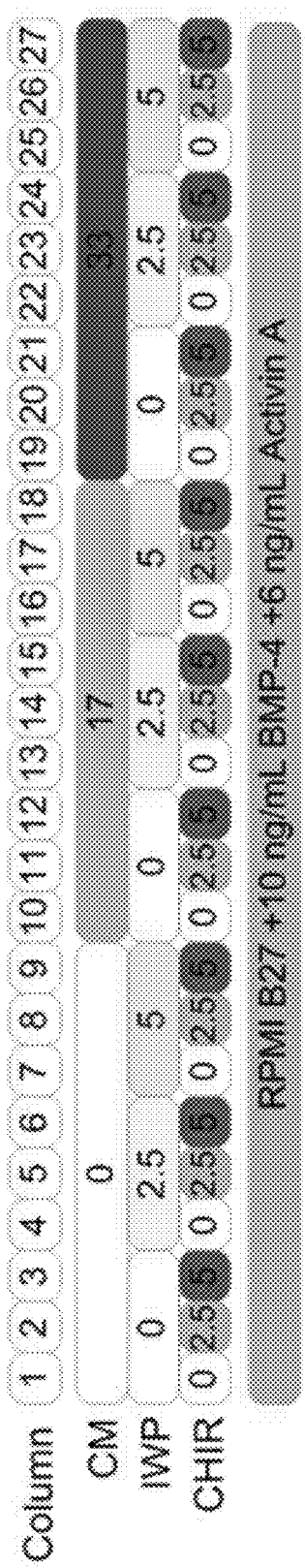
FIG. 7A is a diagram of a second example of screening conditions used for screening of HES3-MIXL1-GFP cells for induction of primitive streak marker MIXL1 and modulation of paracrine effects, using the apparatus of FIGS. 3A to 3C.
Figure 7B:
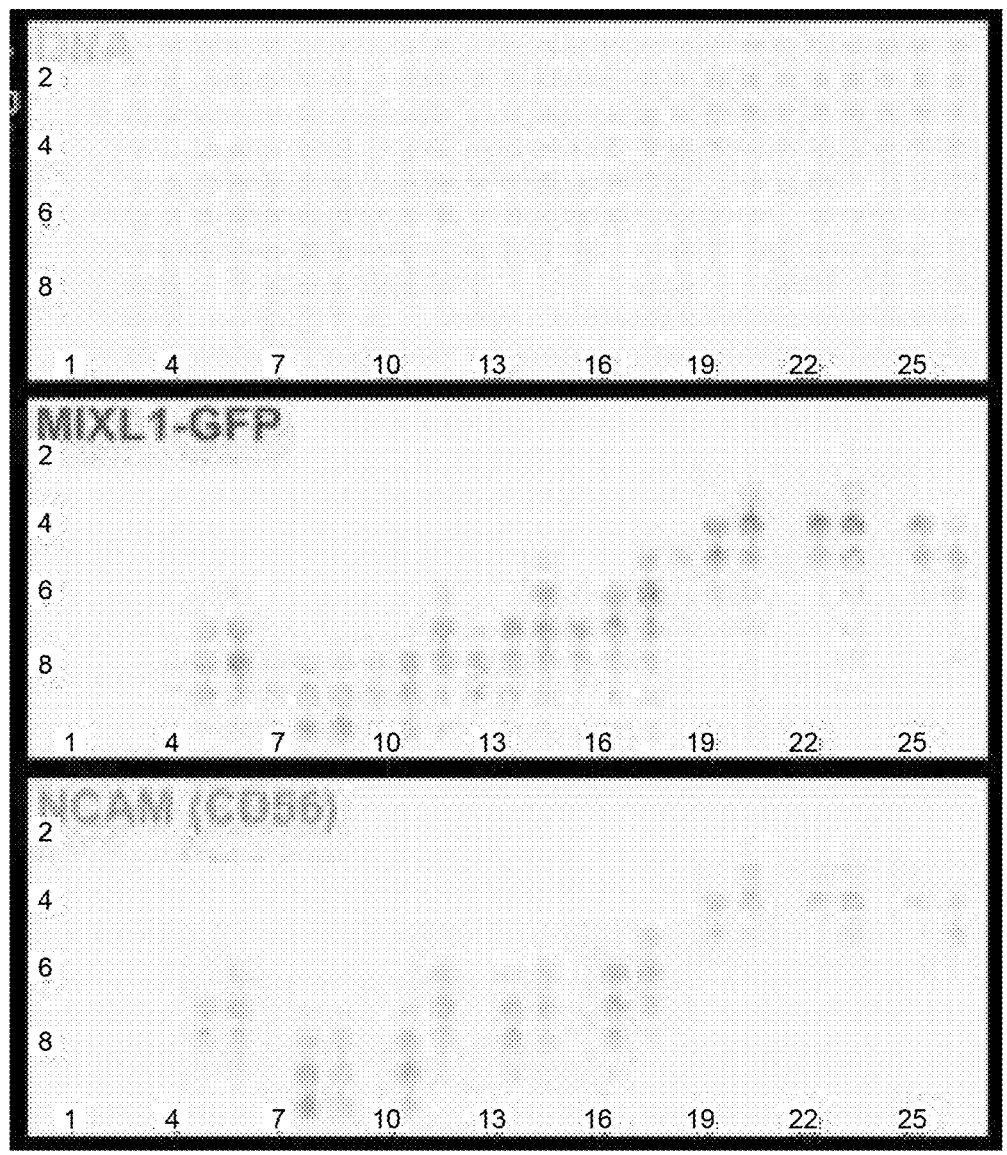
FIG. 7B is an example of a laser scanning confocal negative image of the well array for HES3-MIXL1-GFP hESCs expressing GFP and co-immunostained in situ for NCAM (CD56) and counterstained with Hoechst at experiment endpoint for the screening conditions of FIG. 7A.

FIG. 7A shows the screening conditions used, with numbers indicating concentrations of CHIR99021 (CHIR, μM), induction-conditioned and factor-supplemented medium (CM, final % v/v) and IWP-4 (μM). A confocal tile scan image of HES3-MIXL1-GFP hESCs expressing GFP and counterstained with Hoechst at experiment endpoint is shown in FIG. 7B, with heatmaps of total fluorescence intensities in the array being shown in FIG. 7C.

Figure 7C:
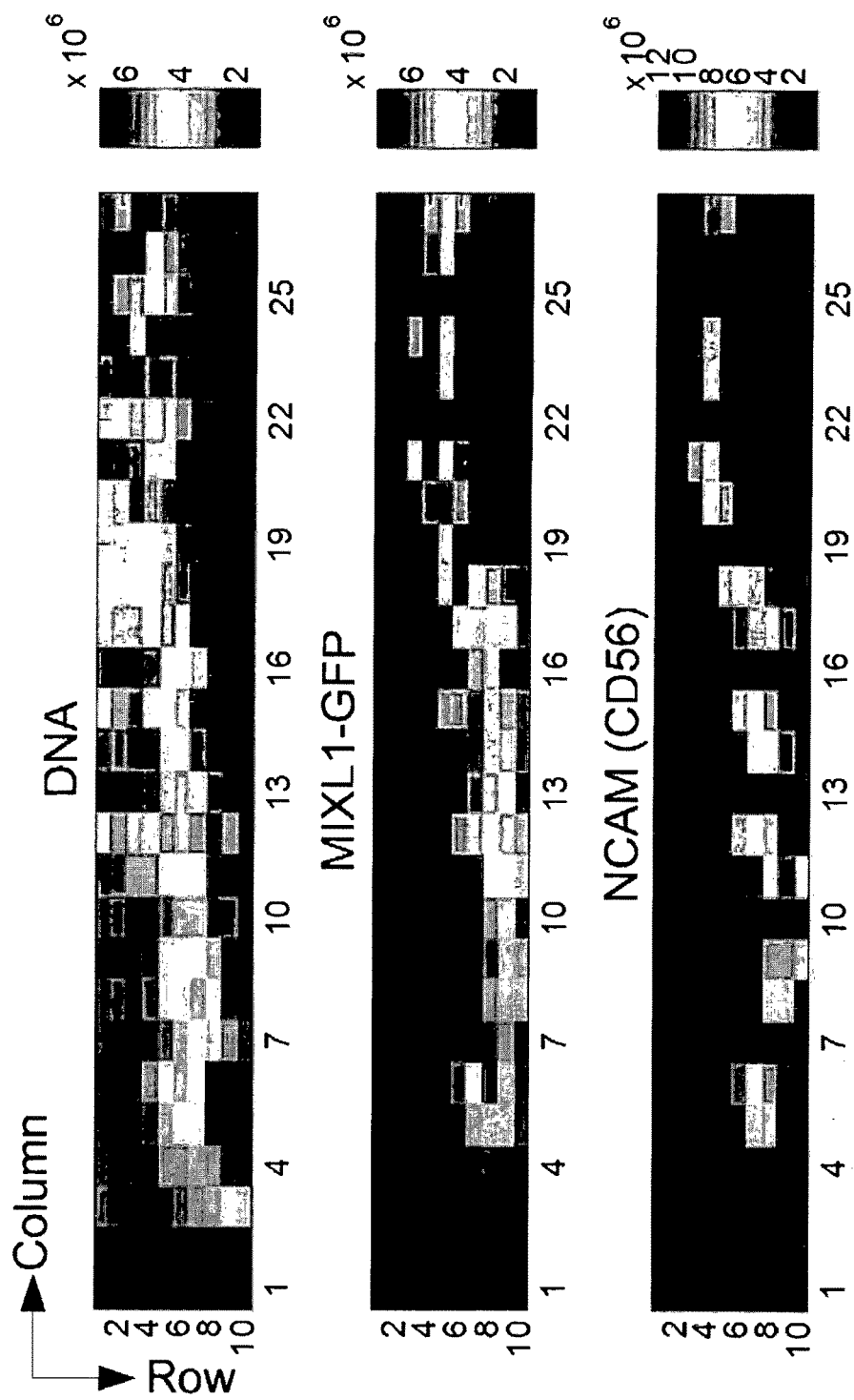
FIG. 7C shows example heatmaps of total fluorescence intensities in the array for the screening conditions of FIG. 7A.
Figure 7D:
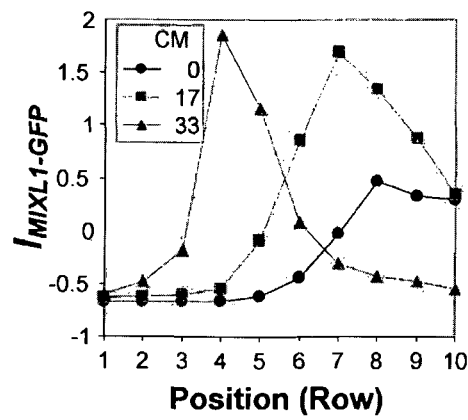
FIGS. 7D to 7G are graphs of example responses in different wells for different conditions.
Figure 7E:
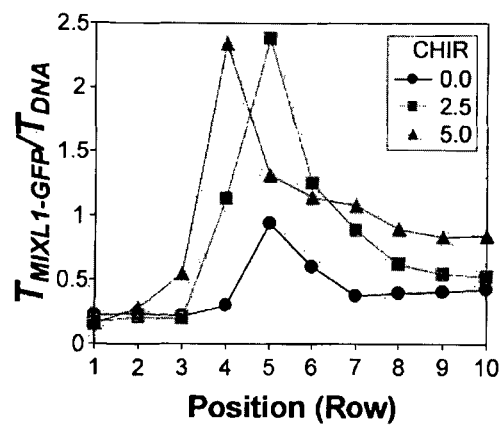
Figure 7F:
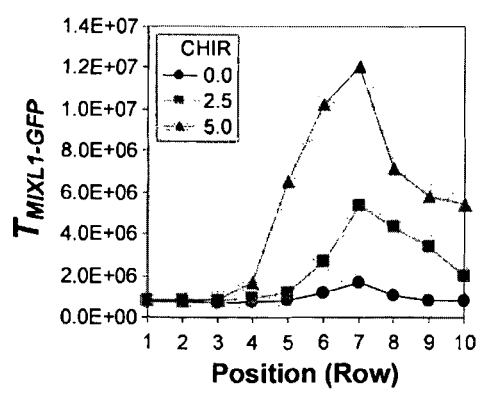
Figure 7G:
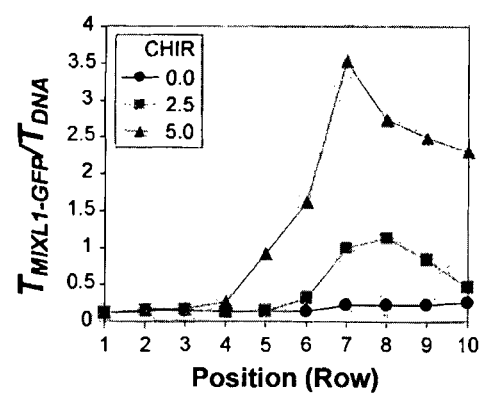

FIG. 7D is a plot of interaction effects showing average effect magnitudes for combinations of CM and Position on IMIXL1-GFP. This highlights that conditioned medium both improved the expression level and shifted the expression towards the top of the array. In FIG. 7E shows DNA-normalised total fluorescence intensities (TMIXL1-GFP/ TDNA) for columns 19-21 showing position-dependent effect of CHIR addition. CHIR both improved the expression level and broadened the number of rows over which appreciable expression extended. FIGS. 7F and 7G show data from a separate array run confirming effect of CHIR addition, in terms of total and DNA-normalised intensities respectively.

Figure 7H:
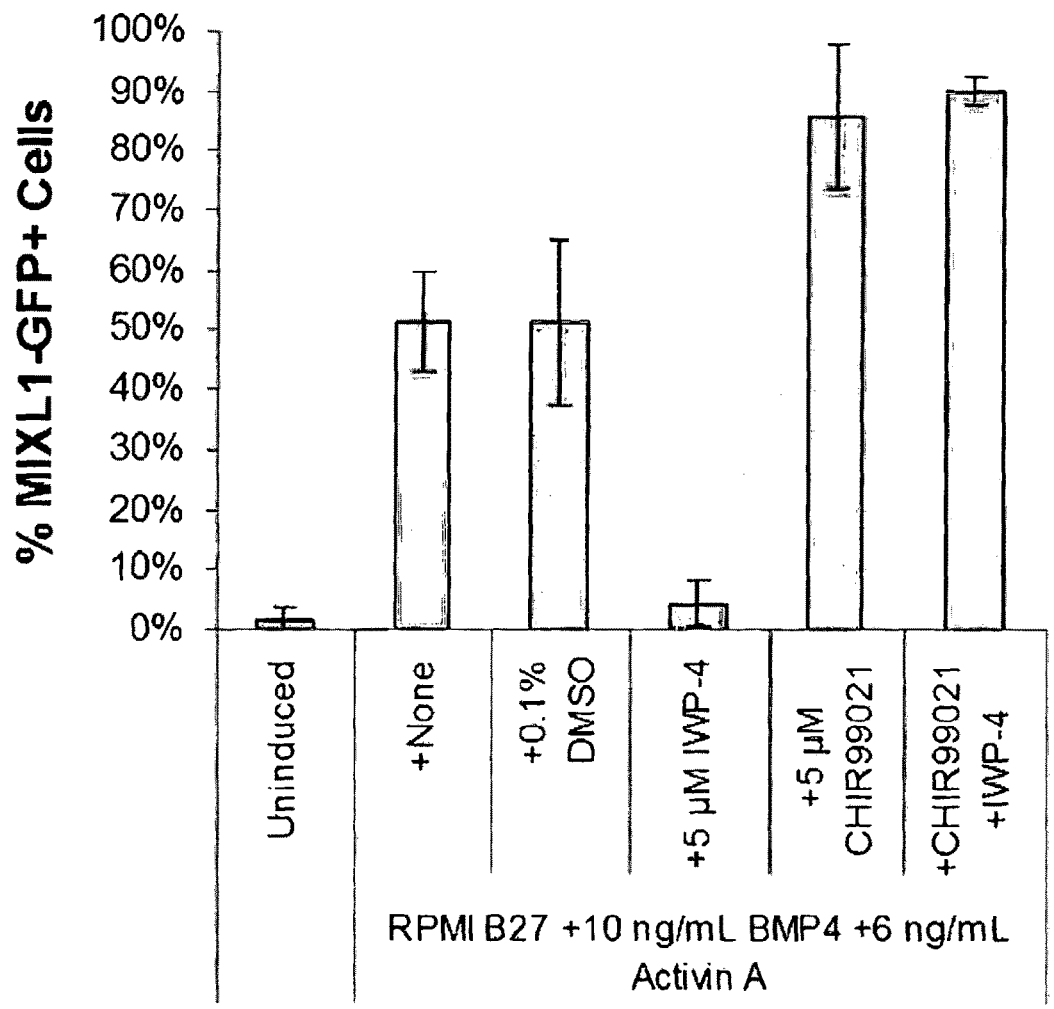
FIG. 7H is a graph of examples of Chemical modulation of Wnt signals and improvement of efficiency in static primitive streak induction cultures for the screening conditions of FIG. 7A.

FIG. 7H shows Wnt accumulation is also required as IWP-4 completely blocked MIXL1 induction in static controls, however is not likely the "limiting" accumulated factor, as CHIR99021 only shifted expression up marginally.

Subsequent to MIXL1-GFP activation, expression intensity was attenuated rapidly in downstream culture wells, indicating that MIXL1 induction is either regulated by a narrow concentration range of paracrine factors, or that the MIXL1-GFP$^+$ population itself produces factors which feedback negatively on its induction.

It was also noted that in one of the conditions, column 15 (10 ng/mL BMP-4, 6 ng/mL Activin A, 1 μM BIO), bright MIXL1-GFP expression extended over 4-5 rows, rather than the single peak of fluorescence seen at row 7 in column 6 (under identical conditions but without BIO) as shown in FIGS. 5B and 5C. This suggested that that the negative feedback effect could in part be overcome by enforced canonical Wnt signalling. To test this hypothesis, cells were differentiated in a full-factorial array of CHIR99021 (CHIR, a GSK-3β inhibitor that, in contrast to BIO, does not interfere with CDK4 activity), induction-conditioned medium re-supplemented with 50% of nominal levels of BMP-4 and Activin A (CM), and IWP-4 (an inhibitor of Wnt production) in a background of RPMI B27 medium containing 10 ng/mL, BMP-4 and 6 ng/mL Activin A (Supplementary Methods). CHIR99021 likewise produced an extended streak of MIXL1-GFP expression, as shown in FIGS. 7B, 7C, 7E, which based on its mode of action—intracellular enforcement of canonical Wnt signalling at the GSK-3β/β-catenin level—implicates secreted Wnt-antagonistic signals such as DKKs and sFRPs as a class of potential mediators of this feedback loop. This effect was also pronounced in a separate array experiment shown in FIGS. 7F, 7G.

Although such paracrine factor dependencies and negative feedback signals regulating mesendoderm specification are clearly necessary developmental drivers in a transient in vivo structure such as primitive streak, they inevitably reduce efficiency of in vitro differentiation. It was therefore tested whether the outcomes of modulating positive and negative paracrine regulators in the array could be translated to optimise directed differentiation protocols in conventional static cultures. Indeed, it was found that relative to standard conditions of RPMI B27+10 ng/mL BMP-4+6 ng/mL Activin A, addition of 5 μM CHIR99021 increased MIXL1-GFP induction from 51% to 86% of cells, as shown in FIG. 7H.

A further specific example of apparatus will now be described with reference to FIGS. 8A to 8D, which shows a modified version of the apparatus of FIGS. 3A to 3C.

In this example, the apparatus again includes first and second cover layers 801, 802, shown in FIGS. 8A and 8A, mounted to a substrate 803. Again, the layers may be formed form PDMS or other similar materials, bonded using a suitable bonding process. The substrate is typically adapted to cooperate with a slide holder to provide a standard microplate footprint, as described in the previous example of FIGS. 3A to 3C.

In this example, the apparatus 800 includes inlets 810, interconnected via channels 820 to the well array 830. The inlets 810 are provided in the first layer 801 and connected to the well array in the second layer 802, via respective ports. It will be appreciated that this arrangement is similar to that of the previous specific example of FIGS. 3A to 3C and will not therefore be described in any further detail.

In this example, the apparatus includes four pairs of inlets 811.1, 811.2, 812.1, 812.2, 813.1, 813.2, 814.1, 814.2, with each pair of inlets being for receiving a respective factor and buffer. The well array 830 defines a full-factorial array composed of 3 concentration levels, of 4 factors, supplied via the four pairs of inlets, over 81 well channels. The channels are replicated twice in the well array. Each well channel includes 50 wells, thereby defining a well array with eight thousand one hundred wells.

Figure 8C:
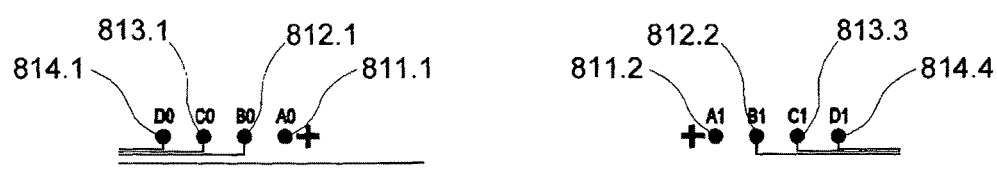
FIG. 8C is a schematic diagram of a further specific example of first layer.
Figure 8D:
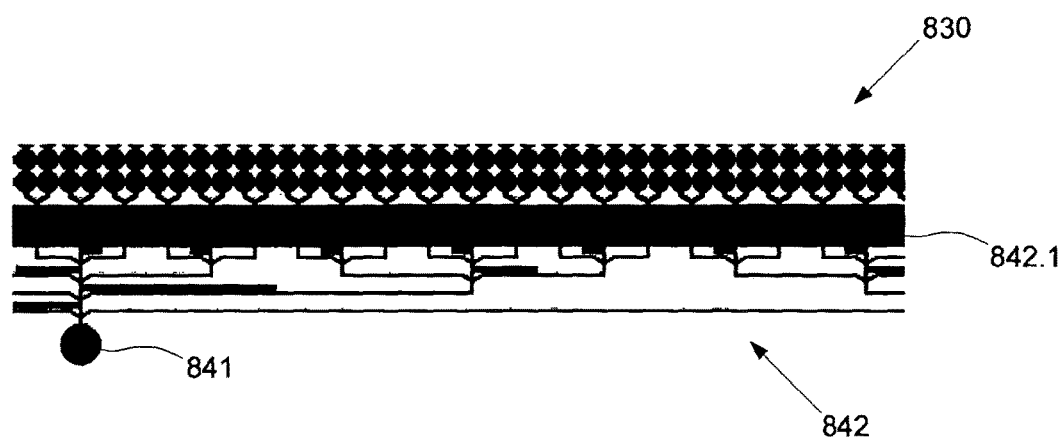
FIG. 8D is a schematic diagram of a further specific example of second layer.

As shown in FIG. 8C, the four pairs of inlets 811.1, 811.2, 812.1, 812.2, 813.1, 813.2, 814.1, 814.2 are provided aligned on the second layer, though suitable re-routing of the channels. Providing the inlets in an aligned configuration assists with coupling the inlets to fluid supplies, for example by allowing a single clip connector to be used to coupled factor and buffer supplies to the inlets as required. In one example, this can be used to accommodate a Dolomite Microflux Connector (8-pin) layout.

To ensure consistent delivery of factors and buffers to the well channels, the resistances of the channels 320 are redesigned accordingly, for example through the use of suitable tortuousities.

The apparatus 800 further includes a seeding inlet 841, which can be used for receiving a seeding fluid containing the cells. The seeding inlet is in fluid communication with the well channels via seeding channels 842, which are typically connected to an end of the well channels opposite to the connection point for the channels 820. It will be appreciated that this allows the seeding inlet to also function as an outlet, allowing fluid that has flowed though the well channels to be expelled as required.

In this example, the seeding channels 842 are provided in an equal-resistance (fractal) arrangement to improve flow-rate distribution. Additionally, a low resistance channel 842.1 of increased width is provided. The inclusion of an equal-resistance seeding channels acting as outlet section ensures uniform flow distribution during operation, as well as providing a low-resistance cell seeding structure for even cell distribution during seeding.

Additionally, the provision of longer channels in the outlet section provides a diffusion barrier between the cell seeding structure and the well channel array to prevent cross contamination of well channels in use.

Figure 8E:
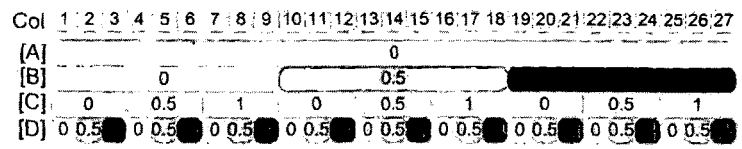
FIG. 8E is a schematic diagram of the theoretical concentrations of each of factors A, B, C, D in the apparatus of FIGS. 8C and 8D.
Figure 8E:
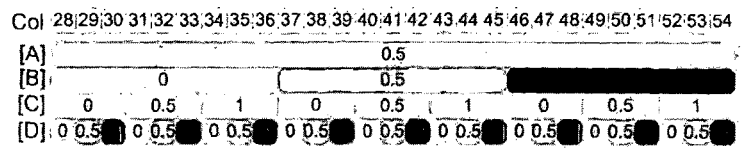
Figure 8E:
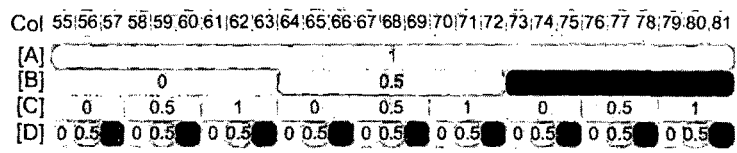
Figure 8F:
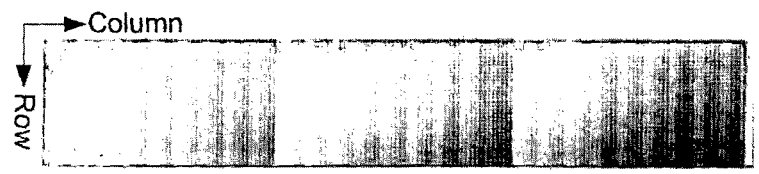
FIG. 8F is a schematic diagram of the resulting dye distribution in the apparatus of FIGS. 8C and 8D using four colours to represent each of factors A, B, C, D.
Figure 8G:
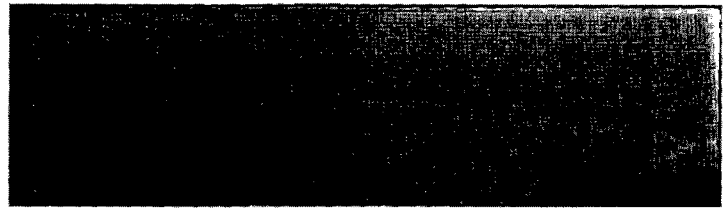
FIG. 8G is a schematic diagram of the resulting dye distribution of a single coloured dye supplied via the outlet; and, FIG. 8H is an image of the apparatus of FIGS. 8C and 8D in use.
Figure 8H:
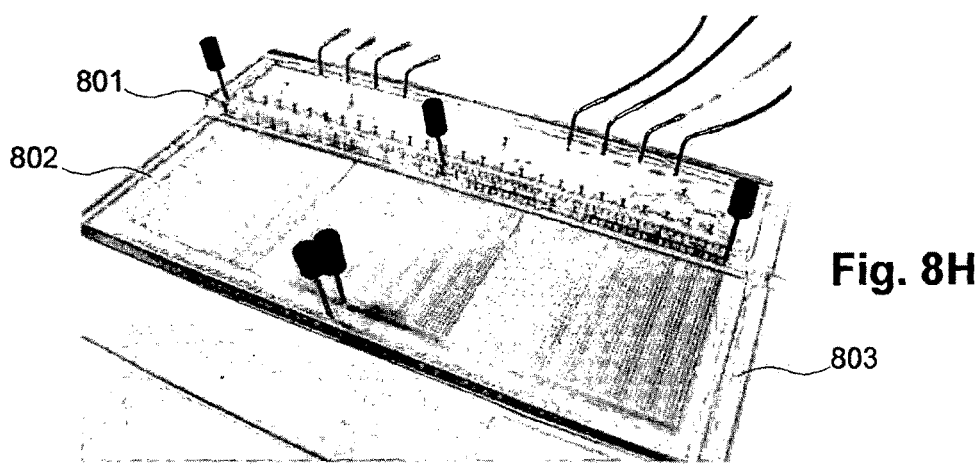
FIG. 8A is a schematic diagram of a further specific example of an inlet configuration.
FIG. 8B is a schematic diagram of a further specific example of an outlet configuration.

An example of the combination of factors across each of the eighty one well channels is shown in FIGS. 8E and 8F, with green, red, yellow and blue dyes being used to simulate factors A, B, C, D provided to the inlets 811.1, 812.1, 813.1, 814.1, with corresponding buffers provided to the inlets 811.2, 812.2, 813.2, 814.2. In this example, the theoretical concentrations are shown in FIG. 8E with the actual resulting concentrations from dye-loading experiments being shown in FIG. 8F. Additionally, the results of dye loading via the seeding inlet 841 is shown in FIG. 8G, which highlights even distribution of dye throughout the well channel.

Accordingly, the above described examples provide apparatus for modulating cell activity under a variety of conditions. In one example, apparatus utilises a defined medium and attachment substrate for uncompromised screening of soluble factors, provides continuous perfusion of medium to separate and visualise paracrine effects and present a more temporally-stable microenvironment, and generates a full-factorial complement of culture conditions to deconvolute interaction effects between multiple stimuli.

Experimental data demonstrate that the apparatus can be utilised to map defined combinations of stimuli to phenotypic outcomes in pluripotent stem cells across a wide range of processes. Additionally, the array is capable of spatially separating and visualising paracrine effects which are masked in conventional static cultures, and particularly EBs, through the provision of a plurality of wells positioned along the well channel. By revealing paracrine signatures resulting from a given exogenous factor stimulation regime, the device also provides an assay for decoding the hierarchy of direct-acting soluble factors: the direct addition of putative paracrine factors to the array, as well as depletion of factors from the medium or inhibition of their signalling pathways, are effective strategies to reveal the identity of paracrine factors involved in driving differentiation outcomes, for example.

The apparatus also allows paracrine effects that modulate differentiation outcomes to be examined, allowing identification of hierarchy and mode of action, or specific factors responsible.

It will be appreciated that the above described apparatus could be used with a standardised platform architectures with automation and peripheral support of microfluidic chips, to allow for the broad application of microbioreactor array technology to discovery and optimisation of microenvironmental signals controlling pluripotent stem cell self-renewal and differentiation processes, ultimately unlocking the future potential of pluripotent stem cells. The platform may also have broad utility for other cell types as a universal microenvironmental screening platform for various biomolecules and pharmacological agents.

A variety of substances are contemplated, including, but not limited to a promoter, an inhibitor, a growth factor, a clotting factor, a hormone, a signalling agent, chemical compositions, a drug, a protein, a ligand, an antibody, an organism, cells, mini-cells, synthetic cells, a liposome, a micelle, a polymeric micelle (polymersome), a lipid, a polymer, a surfactant, a fatty acid, an ionic solution, an acidic or basic solution, a detection reagent, a DNA molecule, an RNA molecule, a construct encoding a DNA or RNA sequence, a nucleotide, a nucleoside, a polypeptide, an amino acid, a viral particle, a plasmid, a nanoparticle, a microparticle, a magnetic particle, conditioned medium, a fraction purified from conditioned medium, a natural extract, a culture medium component, a cell culture additive, a carbohydrate, a vitamin, a metabolite, an oligonucleotide, a fusion protein, a proteoglycan and a pathogen.

In terms of cells that can be used, non-limiting examples of include: stem cells including, but not limited to, haematopoietic stem cells, neural stem cells, bone stem cells, muscle stem cells, mesenchymal stem cells, epithelial stem cells, endodermal stem cells, pluripotent embryonic stem cells, induced pluripotent stem cells, pluripotent embryonic germ cells, totipotent cells; myoblasts; neutrophils; lymphocytes; mast cells; erythroblasts; osteoblasts; osteoclasts; chondrocytes; basophils; eosinophils; adipocytes; neurons; adrenomedullary cells; melanocytes; epithelial cells; endothelial cells; hepatocytes; lung cells; renal cells; and precursors respectively thereof; tumour cells, illustrative examples of which include: melanoma, myeloid leukemia, carcinomas of the lung, breast, ovaries, colon, kidney, prostate, pancreas, brain and testes; intermediate populations of progenitor or differentiated cells derived from stem cells or other cells; and, mixtures of cells composed of any of the above. Other suitable cells include known research cells and cell lines including, but not limited to, Jurkat T cells, NIH3T3 cells, CHO, COS, etc, as well as non-mammalian cell types including bacteria, algae, yeast, fungi, etc. In some embodiments, the cells form a substantially homogeneous population of cells. In other embodiments, the cells form a heterogeneous culture and include cell types that are known to interact via paracrine signalling mechanisms.

A variety of coatings are contemplated, including, but not limited to a promoter, an inhibitor, a growth factor, a clotting factor, a hormone, a signalling agent, chemical compositions, a drug, a protein, a ligand, an antibody, an organism, cells, mini-cells, synthetic cells, a liposome, a micelle, a polymeric micelle (polymersome), a lipid, a polymer, a surfactant, a fatty acid, an ionic solution, an acidic or basic solution, a detection reagent, a DNA molecule, an RNA molecule, a construct encoding a DNA or RNA sequence, a nucleotide, a nucleoside, a polypeptide, an amino acid, a viral particle, a plasmid, a nanoparticle, a microparticle, a magnetic particle, conditioned medium, a fraction purified from conditioned medium, a natural extract, a culture medium component, a cell culture additive, a carbohydrate, a vitamin, a metabolite, an oligonucleotide, a fusion protein, a proteoglycan and a pathogen.

The fluids can also include agents, including, but not limited to a promoter, an inhibitor, a growth factor, a clotting factor, a hormone, a signalling agent, chemical compositions, a drug, a protein, a ligand, an antibody, an organism, cells, mini-cells, synthetic cells, a liposome, a micelle, a polymeric micelle (polymersome), a lipid, a polymer, a surfactant, a fatty acid, an ionic solution, an acidic or basic solution, a detection reagent, a DNA molecule, an RNA molecule, a construct encoding a DNA or RNA sequence, a nucleotide, a nucleoside, a polypeptide, an amino acid, a viral particle, a plasmid, a nanoparticle, a microparticle, a magnetic particle, conditioned medium, a fraction purified from conditioned medium, a natural extract, a culture medium component, a cell culture additive, a carbohydrate, a vitamin, a metabolite, an oligonucleotide, a fusion protein, a proteoglycan and a pathogen. The agents can be in any suitable form, such as dissolved within the fluid, or suspended as a solid within the fluid.

Accordingly, the above described examples provide a scalable, continuous-flow microbioreactor array that present a full-factorial set of exogenous modulating agents, and additionally allow accumulation of endogenous modulating agents along a separate dimension. Using examples of pluripotency maintenance and primitive streak differentiation in human embryonic stem cells the above described experiments demonstrate the unique ability of this platform to separate, visualise, identify and modulate paracrine effects not readily accessible in conventional culture platforms. The array platform decodes factor interplay and the hierarchy of direct-acting soluble factors and paracrine signalling events, and therefore allows for deciphering micro-environmental control, such as factor effects, on stem cell fate.

In one particular example, the array generates all combinations of 3 concentrations each of 3 soluble factors (a full-factorial array; $3^3=27$ distinct conditions in total), using only 6 fluidic inputs and allows identification of optimum treatments, interaction effects between factors, and separation of paracrine factor accumulation and subsequent visualisation of differential effects on cell phenotype. The array can be coated with various attachment substrata and sustain hESCs with continuous slow perfusion of culture media for at least 7 days. Reporter gene expression and/or in situ immunostaining allows readout of cell phenotypes.

It will be appreciated that the above described apparatus can be used in any scenario in which it is desired to be able to assess the response of substances to different conditions, and in particular assess the response of a cell to different environmental conditions, for example through exposure to cell modulating agents. The apparatus can therefore be applied to a range of applications and modulating agents. For example, the apparatus can be used for culturing, incubating, reacting, assaying and differentiating cells, as well as for performing tests on modulating agents, for example to test the effectiveness of a drug at altering cell activity. Other monitoring can include cell viability, cell morphology, cell signalling, protein translocation, cell antigen presentation, DNA synthesis, cell genome, cell transcriptome, cell proteome, cell metabolism, cell electrophysiological function, cell physiological function, phagocytosis, endocytosis, gene expression, protein expression, carbohydrate expression, biomolecular interactions, receptor binding, cell binding of a detection agent and cell uptake of a modulation agent.

The above described examples are not therefore intended to be limiting.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. An apparatus for exposing a substance to conditions, the apparatus including:
   a) an array of wells including a number of well channels, each well channel including a plurality of wells spaced apart along the well channel, the wells containing a substance in use;
   b) a plurality of inlet sets, each inlet set including first and second inlets that receive respective first and second fluids, each inlet set receiving a respective first fluid; and,
   c) channels coupled to the inlets for selectively supplying one or more fluids to each well channel to thereby expose the substance to different conditions allowing a response of the substance to the conditions to be determined, wherein each channel divides to supply fluid to at least two well channels and wherein at least two channels combine to supply a mixture of fluids to at least one well channel; and,
   d) a substrate and a cover layer, wherein the cover layer includes a first and second layer, and wherein the wells are defined in at least one of the substrate and the cover layer, and wherein:
      i) the cover layer includes ports that connect channels in the second layer to channels in the first layer;
      ii) at least one inlet set is provided in the second layer, wherein each inlet in the at least one inlet set is connected to multiple ports via respective channels in the second layer, and wherein each port is connected to a respective channel in the first layer; and,
      iii) at least some of the respective channels in the first layer combine with other channels in the first layer, wherein at least one of the other channels in the first layer is connected to an inlet of another inlet set.

2. The apparatus according to claim 1, wherein the apparatus includes a number of channels for supplying the respective fluids from the inlets to the well channels, each channel having a respective channel geometry to thereby control a relative flow of fluids so that respective proportions of the fluids are supplied to each well channel.

3. The apparatus according to claim 1, wherein the fluid supplied to a first end of the well channel flows along the well channel to a second end of the well channel in a flow direction and wherein at least one of:
   a) a response in at least one well influences conditions in an adjacent well; and,
   b) at least some agents produced in a well are transferred to an adjacent well to thereby at least partially alter the conditions in the adjacent well.

4. The apparatus according to claim 1, wherein a well channel geometry of each channel is arranged so that each well channel receives at least one of:
   a) an equal volume of fluid;
   b) an equal flow of fluid; and,
   c) equal proportions of fluid and wherein the channel geometry includes at least one of:
      i) a channel shape;
      ii) a channel tortuousity;
      iii) a channel length;
      iv) a channel height;
      v) a channel width;
      vi) a channel angle; and,
      vii) obstructions within the channel.

5. The apparatus according to claim 1, wherein the channels include mixing portions for mixing fluids contained therein and wherein at least two channels combine upstream of a mixing portion.

6. The apparatus according to claim 1, wherein the first fluid includes a factor and the second fluid includes a buffer, and wherein the channels are arranged so that:
   i) at least one well channel receives the first fluid;
   ii) at least one well channel receives the second fluid; and,
   iii) at least one well channel receives a mixture of the first and second fluids.

7. The apparatus according to claim 1, wherein each inlet sets receives a fluid including a respective factor.

8. The apparatus according to claim 1, wherein the apparatus includes:
   a) a number (n) of inlet sets, each including at least two inlets, resulting in a total of at least 2n inlets; and,
   b) a number (n) of inlet sets, each containing at least 2 inlets, where 1 inlet from each inlet set is further joined to a common inlet, resulting in a total of at least n+1 inlets.

9. The apparatus according to claim 1, wherein the apparatus includes:
   a) a first inlet set for receiving a first factor and a buffer;
   b) a second inlet set for receiving a second factor and a buffer;
   c) a third inlet set for receiving a third factor and a buffer and wherein each well channel receives a respective concentration of each of the first, second and third factors.

10. The apparatus according to claim 1, wherein the fluids from one inlet set are combined by mixing with the fluids of a subsequent inlet set, thereby combining the respective fluids.

11. The apparatus according to claim 1, wherein the apparatus includes:
    a) at least one seeding inlet for receiving a seeding fluid containing the substance; and,
    b) at least one seeding outlet, the at least one seeding inlet and seeding outlet being in fluid communication with the well channels, thereby allowing the wells to be seeded with the substance.

12. The apparatus according to claim 11, wherein at least one of:
    a) the apparatus includes a number of seeding channels for connecting at least one of the at least one seeding inlet and the at least one seeding outlet to the well channels;
    b) the at least one seeding inlet is connected to an opposing end of the well channels to the at least one seeding outlet; and,
    c) the seeding outlet is in fluid communication with the channels, and wherein the seeding outlet is arranged to be blocked after seeding of the well channels, thereby allowing the respective fluids to be supplied to the well channels.

13. The apparatus according to claim 1, wherein the apparatus includes at least one control device for selectively controlling at least one of:
    a) supply of fluid to at least one of a well channel and a well; and,
    b) sampling of fluid and/or substances from at least one of a well channel and a well.

14. The apparatus according to claim 13, wherein the control device includes a valve for selectively blocking a channel.

15. The apparatus according to claim 1, wherein the cover layer includes a moulded polymeric material.

16. The apparatus according to claim 1, wherein the substrate and cover layer are coupled using at least one of:
   a) adhesive coupling;
   b) thermal coupling;
   c) mechanical coupling;
   d) plasma coupling;
   e) covalent/chemical coupling;
   electrostatic coupling; and,
   g) magnetic coupling.

17. The apparatus according to claim 1, wherein at least the wells are coated.

18. The apparatus according to claim 17, wherein the coatings include at least one of:
   a) a promoter;
   b) an inhibitor;
   c) a growth factor;
   d) a clotting factor;
   e) a hormone;
   a signalling agent;
   g) chemical compositions;
   h) a drug;
   i) a protein;
   j) a ligand;
   k) an antibody;
   l) an organism;
   m) cells;
   n) mini-cells;
   o) synthetic cells;
   p) a liposome;
   q) a micelle;
   r) a polymeric micelle (polymersome)
   s) a lipid;
   t) a polymer;
   u) a surfactant;
   v) a fatty acid;
   w) an ionic solution;
   x) an acidic or basic solution;
   y) a detection reagent;
   z) a DNA molecule;
   aa) an RNA molecule;
   bb) a construct encoding a DNA or RNA sequence;
   cc) a nucleotide;
   dd) a nucleoside;
   ee) a polypeptide;
   ff) an amino acid;
   gg) a viral particle;
   hh) a plasmid;
   ii) a nanoparticle;
   jj) a microparticle;
   kk) a magnetic particle;
   ll) conditioned medium;
   mm) a fraction purified from conditioned medium;
   nn) a natural extract;
   oo) a culture medium component;
   pp) a cell culture additive;
   qq) a carbohydrate;
   rr) a vitamin;
   ss) a metabolite;
   tt) an oligonucleotide;
   uu) a fusion protein;
   vv) a proteoglycan; and,
   ww) a pathogen.

19. The apparatus according to claim 1, wherein at least one channel in the second layer crosses over at least one channel in the first layer.

20. The apparatus according to claim 1, wherein the apparatus includes a channel network in each of the first and second layers.

* * * * *